United States Patent
Brass et al.

(10) Patent No.: US 9,599,563 B2
(45) Date of Patent: Mar. 21, 2017

(54) LED INSPECTION LAMP AND LED SPOTLIGHT

(76) Inventors: Jack Brass, North York (CA); Richard J. Doran, Kent (GB); Donald L. Klipstein, Upper Darby, PA (US); Thomas M. Lemons, Marblehead, MA (US); Bjarki Hallgrimson, Ottawa (CA); Sarah Dobbin, Ottawa (CA)

( * ) Notice: Subject to any disclaimer, the term of this patent is extended or adjusted under 35 U.S.C. 154(b) by 718 days.

(21) Appl. No.: 12/503,304

(22) Filed: Jul. 15, 2009

(65) Prior Publication Data

US 2010/0008079 A1      Jan. 14, 2010

Related U.S. Application Data

(63) Continuation of application No. 11/695,894, filed on Apr. 3, 2007, now Pat. No. 7,568,816, which is a
(Continued)

(51) Int. Cl.
G01N 21/64 (2006.01)
G01N 21/31 (2006.01)
G01N 21/88 (2006.01)

(52) U.S. Cl.
CPC ......... *G01N 21/6428* (2013.01); *G01N 21/31* (2013.01); *G01N 21/6402* (2013.01);
(Continued)

(58) Field of Classification Search
USPC ....... 362/208, 230, 244, 248, 231, 237, 240, 362/184
See application file for complete search history.

(56) References Cited

U.S. PATENT DOCUMENTS 1,507,742 A    9/1924  Kollath
2,469,080 A    5/1949  Rosin
(Continued)

FOREIGN PATENT DOCUMENTS

CA    2200364 AA    5/1997
CA    2200365 AA    5/1997
(Continued)

OTHER PUBLICATIONS

Two Pole Two Position Switch, Nov. 1969, vol. 12, No. 6, p. 747 (IBM Technical Bulletin).*
(Continued)

*Primary Examiner* — Sharon Payne
(74) *Attorney, Agent, or Firm* — Dentons US LLP; Brian R. McGinley

(57) ABSTRACT

An LED inspection lamp has plurality of LED sources for emitting electromagnetic radiation at different peak wavelengths for causing visible fluorescence in different leak detection dyes. A lens is associated with each LED. Radiation passing through lenses is superimposed in target area at target distance. Another LED inspection lamp has plurality of LEDs emitting electromagnetic radiation at a peak wavelength. A lens adaptor has lens housing for attachment to LED inspection lamp with a single LED for causing visible fluorescence, and a lens. Substantially all of the radiation from the LED passes through the lens and is focused in a target area at a target distance from the lenses. LED spot lights have a similar configuration. The LEDs may produce white light from distinct LEDs or from white LEDs. The light may be a flashlight or fixed spot light.

21 Claims, 14 Drawing Sheets

Related U.S. Application Data continuation of application No. 10/500,500, filed as application No. PCT/CA02/02020 on Dec. 30, 2002, now Pat. No. 7,204,606, which is a continuation-in-part of application No. 10/029,803, filed on Dec. 31, 2001, now Pat. No. 6,979,104.

(60) Provisional application No. 60/359,656, filed on Feb. 27, 2002.

(52) U.S. Cl.
CPC ..... *G01N 21/6447* (2013.01); *G01N 21/8803* (2013.01); *G01N 2201/0221* (2013.01); *G01N 2201/0612* (2013.01); *G01N 2201/0621* (2013.01); *G01N 2201/0627* (2013.01); *G01N 2201/0638* (2013.01); *G01N 2201/0693* (2013.01); *Y10S 362/80* (2013.01)

(56) References Cited

U.S. PATENT DOCUMENTS

| | | |
|---|---|---|
| 3,379,869 A | 4/1968 | Dorman |
| D215,751 S | 10/1969 | Castellano |
| 3,676,668 A | 7/1972 | Collins |
| 3,808,434 A | 4/1974 | Gutbier |
| 4,013,915 A | 3/1977 | Dufft |
| 4,185,891 A | 1/1980 | Kaestner |
| 4,477,863 A | 10/1984 | Walz |
| 4,826,269 A | 5/1989 | Streifer et al. |
| 4,868,719 A * | 9/1989 | Kouchi et al. ............ 362/545 |
| 4,935,665 A | 6/1990 | Murata |
| 4,963,798 A | 10/1990 | McDermott |
| 5,092,331 A | 3/1992 | Nakamura et al. |
| 5,289,082 A | 2/1994 | Komoto |
| D349,123 S | 7/1994 | Cooley et al. |
| 5,410,453 A | 4/1995 | Ruskouski |
| 5,528,477 A | 6/1996 | Carmo |
| 5,674,000 A * | 10/1997 | Kalley ........................ 362/293 |
| 5,749,830 A | 5/1998 | Kaneko et al. |
| 5,757,557 A | 5/1998 | Medvedev et al. |
| 5,785,404 A | 7/1998 | Wiese |
| 5,806,961 A | 9/1998 | Dalton et al. |
| 5,954,206 A | 9/1999 | Mallon et al. |
| 5,975,712 A | 11/1999 | Shiao |
| 5,984,861 A | 11/1999 | Crowley |
| 6,095,661 A | 8/2000 | Lebens et al. |
| 6,132,072 A | 10/2000 | Turnbull et al. |
| 6,142,650 A | 11/2000 | Brown et al. |
| D434,868 S | 12/2000 | Trigiani |
| 6,165,384 A | 12/2000 | Cooper |
| 6,183,086 B1 | 2/2001 | Neubert |
| 6,190,020 B1 | 2/2001 | Hartley |
| 6,200,134 B1 | 3/2001 | Kovac et al. |
| 6,250,771 B1 | 6/2001 | Sharrah et al. |
| 6,305,818 B1 | 10/2001 | Lebens et al. |
| 6,357,893 B1 | 3/2002 | Belliveau |
| 6,367,949 B1 | 4/2002 | Pederson |
| 6,402,347 B1 | 6/2002 | Maas et al. |
| 6,468,077 B1 | 10/2002 | Melikechi et al. |
| 6,474,851 B1 * | 11/2002 | Baley ........................... 362/477 |
| 6,485,160 B1 | 11/2002 | Sommers et al. |
| 6,491,408 B1 | 12/2002 | Cooper et al. |
| 6,501,084 B1 | 12/2002 | Sakai et al. |
| 6,511,203 B1 | 1/2003 | Winther |
| 6,527,411 B1 | 3/2003 | Sayers |
| D472,890 S | 4/2003 | Suzuki |
| 6,590,220 B1 | 7/2003 | Kalley et al. |
| 6,630,682 B2 | 10/2003 | Shanley et al. |
| 6,637,923 B2 | 10/2003 | Amano |
| D483,508 S | 12/2003 | Galvez |
| D483,893 S | 12/2003 | Galvez |
| 6,710,363 B1 | 3/2004 | Trigiani |
| 6,805,476 B2 | 10/2004 | Amano |
| 6,819,505 B1 | 11/2004 | Cassarley |
| D502,276 S | 2/2005 | Kovacik et al. |
| 6,857,756 B2 | 2/2005 | Reiff |
| 6,866,401 B2 | 3/2005 | Sommers et al. |
| 6,890,086 B2 | 5/2005 | Shiu |
| D509,010 S | 8/2005 | Kovacik et al. |
| 6,940,704 B2 | 9/2005 | Stalions |
| 6,979,104 B2 | 12/2005 | Brass |
| 7,029,150 B2 | 4/2006 | Finch |
| 7,083,297 B2 | 8/2006 | Matthew et al. |
| 7,145,649 B2 | 12/2006 | Brass |
| 7,153,004 B2 | 12/2006 | Galli |
| 7,172,319 B2 | 2/2007 | Holder |
| 7,214,952 B2 | 5/2007 | Klipstein |
| 7,267,466 B2 | 9/2007 | Reiss |
| 2002/0012564 A1 | 1/2002 | Chao |
| 2002/0074559 A1 | 6/2002 | Dowling et al. |
| 2002/0080615 A1 | 6/2002 | Marshall |
| 2002/0093649 A1 | 7/2002 | Brass |
| 2002/0191396 A1 | 12/2002 | Reiff et al. |
| 2003/0007345 A1 | 1/2003 | Cooper |
| 2003/0007346 A1 * | 1/2003 | Cooper et al. ................ 362/184 |
| 2003/0098425 A1 | 5/2003 | Sosinsky |
| 2003/0123254 A1 | 7/2003 | Brass et al. |
| 2003/0142489 A1 | 7/2003 | Cooper |
| 2003/0165065 A1 | 9/2003 | Roller et al. |
| 2003/0169600 A1 | 9/2003 | Amano |
| 2004/0223342 A1 | 11/2004 | Klipstein |
| 2004/0228124 A1 | 11/2004 | Reiff |
| 2005/0007777 A1 | 1/2005 | Klipstein et al. |
| 2005/0083687 A1 | 4/2005 | Brass et al. |
| 2005/0122713 A1 | 6/2005 | Hutchins |
| 2005/0225968 A1 | 10/2005 | Hatherill |
| 2005/0265035 A1 | 12/2005 | Brass |
| 2007/0189019 A1 | 8/2007 | Klipstein |
| 2007/0217188 A1 | 9/2007 | Klipstein |
| 2007/0247844 A1 | 10/2007 | Brass |
| 2007/0253188 A1 | 11/2007 | Klipstein |
| 2008/0198615 A1 | 8/2008 | Klipstein |
| 2008/0212319 A1 | 9/2008 | Klipstein |
| 2009/0147519 A1 | 6/2009 | Klipstein et al. |
| 2009/0161351 A1 | 6/2009 | Klipstein et al. |

FOREIGN PATENT DOCUMENTS

| | | |
|---|---|---|
| CA | 2284870 AA | 9/1998 |
| CA | 2280398 AA | 4/2000 |
| CA | 2405802 AA | 10/2001 |
| CA | 2501477 A1 | 9/2005 |
| DE | 2542220 A | 3/1977 |
| DE | 299574 A | 1/1991 |
| DE | 200 21 934 U1 | 4/2001 |
| DE | 201 10 813 U1 | 9/2001 |
| EP | 0523927 A | 1/1993 |
| EP | 1059202 A | 12/2000 |
| GB | 810256 | 3/1959 |
| WO | 98/39636 A1 | 9/1998 |
| WO | 99/35486 A1 | 7/1999 |
| WO | 01/52605 A | 7/2001 |
| WO | 01/81937 A | 11/2001 |
| WO | 01 81973 A1 | 11/2001 |
| WO | 03/004929 A1 | 1/2003 |
| WO | 03/004932 A1 | 1/2003 |
| WO | 03/025458 A1 | 3/2003 |
| WO | 03/060495 A1 | 7/2003 |
| WO | 2004/107457 A2 | 12/2004 |
| WO | 2006/094390 A1 | 9/2006 |
| WO | 2006/102757 A1 | 10/2006 |
| WO | 2007/128126 A1 | 11/2007 |

OTHER PUBLICATIONS

English Abstract of DD299574.
English Abstract of DE20110813.
Craig Johnson, LEDTronics FlashLED, The LED Museum, http://ledmuseum.home.att.net/tronics.htm, printed Jul. 30, 2004, pp. 1-14, Seattle, WA, USA.

(56) References Cited

OTHER PUBLICATIONS

LEDTronics, Inc., Hi-Power FlashLED Flashlights, www.ledtronics.com, http://netdisty.net/ds/fit-3001/default.asp, date unknown, p. 1, Torrance, CA, USA.

Osram Sylvania, Preliminary data sheet for OS-WL01A, Feb. 25, 2000, pp. 1-4, Germany.

Author Unknown, Cool Blue, Product pages for Dorcy, http://www.dorcy.com/led%20new.htm, printed Feb. 27, 2002, pp. 1-2, Country of publication unknown.

Author Unknown, Hi-power FlashLED Flashlights, Safety LED, http://secure.implex.net/NBAComputers/browse.cfm?CategoryID=8, printed Oct. 12, 2001, p. 1, Country of publication unknown.

Johnson, Craig, LEDTronics Mini-FlashLED, LED Museum, http://ledmuseum.home.att.net/flashled.htm, printed Jul. 30, 2004, pp. 1-7, Seattle, WA, USA.

Sayer Michael, et al. Measurement, Instrumentation and Experiment Design in Physics and Engineering, 2000, pp. 197-198, Prentice-Hall of India, New Delhi, India.

Koller, Lewis R., Ultraviolet Radiation, 2nd ed., Wiley Series in Pure and Applied Optics, 1965, pp. 158-181, John Wiley & Sons, Inc., NY, USA.

Craig Johnson, The LED Museum—LEDs—Gallium Indium Nitrate UV, . . . , http://ledmuseum.home.att.net/index2.htm, printed Jul. 30, 2004, pp. 1-3, Seattle, WA, USA.

Craig Johnson, The LED Museum—LEOs—LED Flashlights—Gallium Indium Nitride UV, . . . , http://ledmuseum.home.att.neUmenutop.htm, retrieved Jul. 30, 2004, pp. 1-15, Seattle, WA USA.

Craig Johnson, LEOs—Galium Indium Nitride UV, . . . , Infinity Task Light, The Punishment Zone, The LED Museum, http://1edmuseum.home.att.neUinfl.htm, Jun. 24, 2002, retrieved Feb. 6, 2006, pp. 1-12, Seattle, WA, USA.

PRIMALEC Limited, Invictalux product brochure, "invictalux a new concept for inspection lamps: a battery powered lamp that you can use for fluorescent leak detection, as well as inspection lighting", http://www.primalec.co.ukfpdfs/invictalux.pdf, 3/3103, pp. 1-2, Kent, UK.

Craig Johnson, Arc Flashlight, The LED Museum, http://home.att.neU-ledmuseum/arclight.htm, Nov. 14, 2006, retrieved 517107, pp. 1-17, Sacramento, CA, USA.

MAXXEON Inc., Maxxeon WorkStar—Cordless Rechargeable LED Work Lights, http://www.maxxeon.comf?gclid=CL2fsZKn-loCFRkeYAodPAt9nw, Apr. 4, 2007, retrieved May 26, 2008, p. 1, Cambridge ON, Canada.

PRIMALEC: find leaks the professional way; "invictalux—The new professional inspection light system for UV fluorescent leak detection, diagnostic, forensic and general inspection", http://www.primalec.co.uklproducts/ultra/invictalux.html, retrieved Aug. 18, 2006, p. 1, Country of publication unknown.

Edmund Optics Inc., TECHSPEC Precision Aspheric Lenses, http://www.edmundoptics.com/onlinecatalog/DisplayProductcfm?productid=2686, Mar. 15, 2007, retrieved Jul. 5, 2007, pp. 1-2, Barrington, NJ, USA.

Edmund Optics Inc., Aspheric Condenser Lenses, http://www.edmundoptics.com/onlinecatalog/displayproductcfm?productID=2454, Mar. 15, 2007, retrieved Jul. 5, 2007, pp. 1-3, Barrington, NJ, USA.

Craig Johnson, Central.Ed. Work Light, The Punishment Zone, The LED Museum, http://ledmuseum.candlepower.us/sixth/clwl.htm, Mar. 5, 2007, retrieved May 26, 2008, pp. 1-8, Sacramento, CA, USA.

LED Lighting Fixtures Inc., LLF : LED Lighting Fixtures: The New Standard in Downlighting, http://ledlightingfixtures.com, Apr. 4, 2007, retrieved May 26, 2008, p. 1, Morrisville, North Carolina, USA.

LED Museum at http://ledmuseum.home.att.net/ledleft.htm printed Feb. 27, 2002.

International Search Report for International Application No. PCT/CA02/02020; mailed on May 16, 2003.

\* cited by examiner

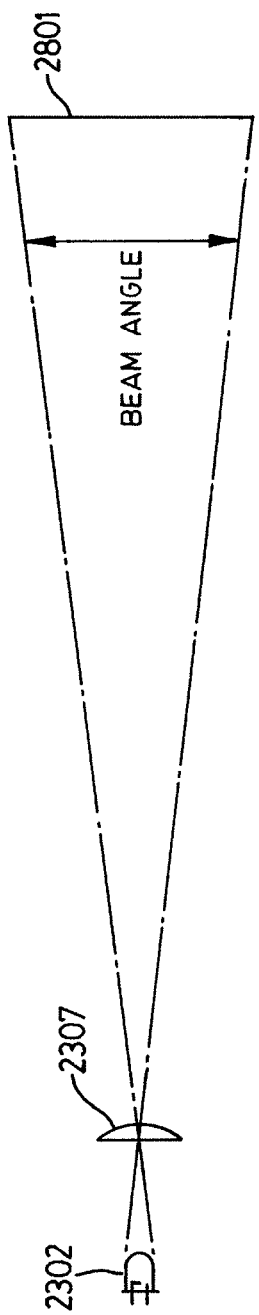

US 9,599,563 B2

LED INSPECTION LAMP AND LED SPOTLIGHT

CROSS-REFERENCE TO RELATED APPLICATIONS

This is a continuation of Ser. No. 11/695,894, filed on Apr. 3, 2007; which is a continuation of Ser. No. 10/500,500, filed Jun. 30, 2004, issued Apr. 17, 2007 as U.S. Pat. No. 7,204,606; which is a §371 of PCT/CA02/02020, filed Dec. 30, 2002; which is a continuation-in-part of Ser. No. 10/029,803, filed Dec. 31, 2001, issued Dec. 27, 2005 as U.S. Pat. No. 6,979,104 and which claims the benefit of 60/359,656 filed Feb. 27, 2002; each of which applications is incorporated herein by reference.

TECHNICAL FIELD

This invention is related to the general field of lighting, and in particular to such lamps having light emitting diodes which produce radiation suitable for exciting fluorescent materials to be detected by such lamps, and in particular to lamps with light emitting diode light sources, and in particular to such lamps having multiple light emitting diodes that produce visible light energy.

BACKGROUND ART

There are many different forms of lighting technology. Incandescent, fluorescent, halogen, HID (high intensity discharge) and light emitting diodes ("LEDs") are a few examples. Incandescent lamps are a low cost relatively inefficient way of providing visible light. Fluorescent lamps are very efficient; however, their light output is relatively low.

Halogen lamps are more efficient than incandescent lamps; but, they run quite hot, still use a fair amount of energy, and emit light over a fairly specific broad spectrum, both visible and invisible. HID lamps provide a substantial amount of light energy in invisible spectra that can be useful in particular applications, such as non-destructive testing. These lamps tend to be large, run very hot, and require warm-up and cool-down time.

There are some products that utilize LEDs. LEDs are very small, run fairly cool, and are very efficient. LEDs are also available in relatively discrete spectra for specific applications requiring spectra limits, such as sources of ultraviolet or specific colours. This allows the use of light sources without filters for these applications. This keeps costs down, simplifies set-up, and improves unit efficiency.

Examples of LED light applications include multiple LEDs grouped in a single head for low power applications, such as a flashlight or a lamp for an alternative energy household. Such lamps often have many LEDs, for example 10 or more, in order to produce enough useful light energy.

Flashlights with light emitting diodes (LEDs) have advantages over flashlights with an incandescent lamp as the light source, especially in performance when the batteries deteriorate. LEDs do not lose efficiency the way incandescent lamps do when the amount of power supplied to the lamp decreases. Another advantage of LED flashlights is greater spectral content in the blue-green and blue wavelengths favorable to night vision compared to flashlights with incandescent lamps.

Others have used single or multiple LED lamps in leak detection applications. These lamps have advantages in size and power consumption; however, they also suffer from relatively low useful light energy.

Detection of leaks in systems containing fluids under pressure is often accomplished by causing visible fluorescence of fluorescent dyes that are added to the fluid in the system. Such systems may be, for example, refrigeration systems where the fluid under pressure is a refrigerant and leakage results in the fluid becoming an invisible gas upon escape. The invisibility of leaked fluid can impair detection of the leak. Addition of a fluorescent dye to the refrigerant allows easier detection of leaks by illuminating possible leakage points with radiation that causes the fluorescent dye to visibly fluoresce at the site of the leak.

Leak detection by means of use of a fluorescent dye is also used in systems other than refrigeration systems, such as automotive cooling systems and in engines having a lubricant that is under pressure.

There are many inspection lamps currently available for the purpose of illuminating potential leak sites with radiation cause visible fluorescence of fluorescent dyes. It is desirable to minimize the size, weight, cost, heat production and power consumption of such inspection lamps while having adequate output from such lamps at wavelengths suitable for causing visible fluorescence of dyes used for leak detection.

Light emitting diodes (LEDs) are used as a source of light for such inspection lamps. LEDs are more efficient at producing desired wavelengths than other light sources used in such inspection lamps. LEDs are also relatively small and produce relatively little heat. Existing LED inspection lamps have had 4 LEDs in an attempt to produce sufficient intensity at a usable distance to make a fluorescent dye fluoresce. For some situations this defeats the purpose of the LED source as additional power must be consumed and the size of the lamp is increased accordingly.

In traditional inspection lamps a broadband light source is utilized, such as an incandescent or halogen bulb. This can have an advantage over LED sources as these sources have a greater radiation output, and they emit radiation over a broad spectrum that can cause a variety of fluorescent dyes to fluoresce. LEDs have a tendency to produce light only in a narrow range of wavelengths.

However, traditional lamps suffer from a number of drawbacks. The broadband light source produces mostly radiation that is not used for detection of any fluorescent dye that has frequent use for leak detection. Also, some of the radiation may be at wavelengths normally emitted by the fluorescent materials to be detected. Filters are typically used to remove such wavelengths from the output of the inspection lamp so that light from the inspection lamp does not mask fluorescence of the fluorescent material to be detected. Radiation absorbed or reflected by filters results in heat, often necessitating means to dissipate this heat.

Alternatively, inspection lamps have been produced using electric discharge light sources since such light sources are often more efficient than incandescent light sources at producing wavelengths suitable for causing visible fluorescence of materials used for leak detection. Such inspection lamps have their own disadvantages such as the cost of the special discharge light sources, the added cost of electrical components required for operation of such light sources, a requirement for some such light sources to spend time warming up to a required elevated operating temperature in order to properly function, and the tendency of many discharge light sources to specialize in production of wavelengths not effectively utilized by all popular fluorescent dyes.

There is a need to derive the full benefit of utilizing LED light sources in inspection lamps. There is also a need to retain some of the benefits of traditional light sources. Further improvements in lighting technology are desirable. It is an object of the invention to address these or other issues associated with LED lamps.

SUMMARY OF THE INVENTION

In a first aspect the invention provides an inspection lamp having light emitting diodes as a source of radiation suitable for causing visible fluorescence of fluorescent materials, where said light emitting diodes are substantially non-identical in spectral characteristics of their emitted radiation, such that at least one but not all of said light emitting diodes in said inspection lamp produce wavelengths of radiation that are favorable for causing visible fluorescence of some fluorescent materials, and such that one or more different said light emitting diodes in said inspection lamp produce substantially different wavelengths of radiation which are more favorable than the wavelengths of first said light emitting diode(s) for causing visible fluorescence of some fluorescent materials other than first said fluorescent materials.

At least one light emitting diode may have a peak emission wavelength in the ultraviolet and at least one light emitting diode may have a peak emission wavelength that is visible but suitable for causing visible fluorescence of fluorescent materials.

At least one light emitting diode may produce mostly blue visible light and at least one light emitting diode may produce mostly visible violet light or ultraviolet radiation.

At least one light emitting diode may have a peak emission wavelength in the range of 425 to 480 nanometers and at least one light emitting diode may have a peak emission wavelength in the range of 360 to 430 nanometers.

The inspection lamp may have one or more lenses to collimate the radiation produced by at least some of the light emitting diodes. The radiation produced by each light emitting diode may be collimated by a separate lens associated with or mounted forward from each said light emitting diode.

The inspection lamp may have a handle. The handle may share a longitudinal axis with the inspection lamp as a whole. The handle may not share an axis with any other major portion of said inspection lamp.

The inspection lamp may accept one or more dry cells as a source of power. The inspection lamp may accept power from an external power source. The external power source may be a source of direct current with a voltage of substantially 12 volts. The external power source may be a source of alternating current with a voltage of substantially 110-125 volts. The external power source may be a source of alternating current with a voltage of substantially 220-240 volts. The inspection lamp may have one or more rechargeable cells as a source of power. The inspection lamp may have means to recharge its rechargeable cells.

The inspection lamp may have one or more dropping resistors to limit the amount of current which flows through at least one of the light emitting diodes. The inspection lamp may have non-switching current regulation means to control the amount of current which flows through at least one of the light emitting diodes. The inspection lamp may have switching current regulation means to control the amount of current which flows through at least one of the light emitting diodes. The inspection lamp may be of such design that at least one of the light emitting diodes does not require separate means to limit or control the amount of current flowing through said light emitting diode.

Any of the light emitting diodes may be laser diodes. The laser diodes may be intended to normally operate in a laser mode. The laser diodes may be intended to normally operate in a non-laser mode. Oblong beams from each laser diode may be directed into different directions so as to achieve an overall beam pattern that is not oblong. The inspection lamp may have optical means to correct oblong characteristics of the beams produced by most types of laser diodes. The inspection lamp may have one more cylindrical lenses to correct oblong characteristic of the laser diodes. The inspection lamp may have optics other than cylindrical lenses to correct oblong beam characteristic of laser diodes. The inspection lamp may be of such design as to produce beams not having the oblong characteristic typical of laser diodes.

In a second aspect the invention provides a module having light emitting diodes that are substantially non-identical and which produce a variety of wavelengths suitable for exciting a variety of fluorescent dyes, and suitable for replacing the bulb and/or the reflector of a flashlight so as to achieve an inspection lamp. The inspection lamp may contain one or more of the modules.

The inspection lamp may have one or more light emitting diode modules, where at least one light emitting diode module has only one type of light emitting diode but the inspection lamp as a whole includes more than one type of light emitting diode so as to produce a variety of wavelengths suitable for exciting a variety of fluorescent dyes. In a third aspect the invention provides an inspection lamp having two or more light emitting diodes that produce radiation suitable for causing visible fluorescence of fluorescent materials, and a lens forward from each of said light emitting diodes to collimate the radiation from each light emitting diode into a beam, such that the beams of radiation individually associated with each of said light emitting diodes project forward from said lenses and merge together.

The individual beams that project forward from each lens may be parallel to each other. The individual beams may converge towards each other such that the axes of the beams intersect with each other at a specific distance forward of the lenses. The individual beams may have an angular diameter greater than any angle between any two axes of said beams, such that some area can be illuminated by all said beams at any distance from the lenses greater than distance from the lenses to the point at which the beam axes intersect.

The lenses may be comprised by a single piece of suitable transparent material. Each lens may have a center of curvature of at least one curved surface displaced from the axis of its associated light emitting diode so as to form a beam having an axis that is not parallel to said axis of said light emitting diode.

A lens assembly may have a longitudinal axis and convex lenses each having at least once curved surface with a center of curvature at a location other than on a line parallel to said lens assembly axis and passing through the center of the area of said lens, so as to be suitable as the lenses of the inspection lamp.

As stated previously for other aspects, the inspection lamp may or may have a handle, and use a variety of internal or external power sources with or without current limiting devices The light emitting diodes may differ significantly in spectral characteristics so as to cause visible fluorescence from fluorescent substances which visibly fluoresce from the output of one or more but not all of said light emitting diodes.

Separate switches may be provided for each type of light emitting diode used within said inspection lamp.

At least one light emitting diode may have a peak wavelength that is ultraviolet and at least one light emitting diode may have a peak wavelength that is visible. At least one light emitting diode may have a peak wavelength less than 425 nanometers and at least one light emitting diode may have a peak wavelength greater than 425 nanometers.

In a fourth aspect the invention provides an LED inspection lamp having a plurality of LED sources. Each source emits electromagnetic radiation at a different peak wavelength. Each different peak wavelength causes visible fluorescence in a different leak detection dye.

A lens may be associated with each LED so that radiation passing through all lenses from their associated LEDs is substantially superimposed to a target area at a target distance from the lenses.

In a fifth aspect the invention provides an LED inspection lamp having a single LED for emitting electromagnetic radiation at a peak wavelength for causing visible fluorescence in a leak detection dye, and a lens associated with the LED so that substantially all of the radiation passes through the lens and is substantially directed to a target area at a target distance from the lenses.

In a sixth aspect the invention provides an LED inspection lamp having a plurality of LEDs emitting electromagnetic radiation at a peak wavelength for causing visible fluorescence in a leak detection dye, and a lens associated with each LED so that the electromagnetic radiation passing through all lenses from their associated LEDs is substantially superimposed to a target area at a target distance from the lenses.

In a seventh aspect the invention provides a lens adaptor having a lens housing for attachment to an LED inspection lamp with a single LED emitting electromagnetic radiation at a peak wavelength for causing visible fluorescence in a leak detection dye, and a lens within the housing. The lens and housing are associated with the LED so that substantially all of the radiation passing through the lens from the LED is substantially directed to a target area at a target distance from the lenses.

In an eighth aspect the invention provides a lens adaptor having a lens housing and lenses. The lens housing is for attaching to an LED inspection lamp with a plurality of LEDs emitting electromagnetic radiation at a peak wavelength for causing visible fluorescence in a leak detection dye. The lenses are for associating with each LED when the lens housing is attached to the inspection lamp. Radiation passing through all lenses from their associated LEDs is substantially superimposed to a target area at a target distance from the lenses.

In a ninth aspect the invention provides a lens and LED assembly for use within a flashlight casing. The assembly has a plurality of LEDs emitting electromagnetic radiation at a peak wavelength for causing visible fluorescence in a leak detection dye, and a lens associated with each LED so that the electromagnetic radiation passing through all lenses from their associated LEDs is substantially superimposed to a target area at a target distance from the lenses. The assembly is shaped to fit within the flashlight casing.

In any of the aspects a lens may be movable to permit adjustment of beam characteristics. The focal length of the lenses and the distance between the lenses (or lens assembly and the light emitting diodes) may be adjustable so as to permit changing the distance at which beam size and intensity formed by each light emitting diode and each associated lens are best-formed.

The distance between lens centers may be smaller than the distance between the centers of their associated light emitting diodes so that the beam components formed by each lens from its associated light emitting diode converge towards each other.

The beam components formed by each lens from its associated light emitting diode may converge towards each other so that all beam components coincide at a distance which can be changed by changing the location of the LEDs.

An inspection lamp may further incorporating means to restrict the possible adjustments to a range of adjustments where the beam elements are best-formed at the same distance forward from said inspection lamp at which said beam elements are coinciding with each other.

In a tenth aspect the invention provides a light producing assembly having two or more light emitting diodes. The assembly also has a lens forward from each of the light emitting diodes such that the light from the light emitting diodes is collimated into a beam.

In an eleventh aspect the invention provides a spot light having two or more light emitting diodes. The spot light also has a lens forward from each of the light emitting diodes such that the light from the light emitting diodes is collimated into a beam.

Each of one or more of the LEDs may be offset from the optical center of its associated lens to cause the radiation passing through the lenses to be substantially superimposed to a target area at a target distance The spot light may have a light producing assembly. The spot light may be suitable for use as a fixed spot light. The spot light may be able to accept as a power source essentially 120 volts alternating current, 230 volts alternating current, 12 volts direct current, or 28 volts direct current, such as from a battery source.

The spot light may be able to accept direct current as a power source. The spot light may be able to accept direct current as a power source and operate even if the polarity of the direct current is reversed.

The spotlight may have light emitting diodes that are essentially identical. The spot light may have light emitting diodes that produce white light. The spot light may have LEDs that produce visible light of different colors. The spot light may have light emitting diodes including red, green and blue light emitting diodes to achieve essentially white light. The spot light may be a flashlight.

The spot light may have light emitting diodes that individually produce light of different colors that combine to form light that is essentially white. The spot light may have orange, blue-green and violet light emitting diodes that are used to achieve essentially white light. The spot light may have yellow, turquoise and magenta or yellow, green and blue light emitting diodes that are used to achieve essentially white light.

The spot light may have light emitting diodes essentially of two complimentary colors that are used to achieve essentially white light. The spot light may have light emitting diodes of more than three distinct colors. The spot light may produce essentially yellow light.

The lenses may be part of a lens assembly that can be moved with respect to the light emitting diodes. The lens assembly may be part of an assembly that slides over the light emitting diodes. The spot light may have a thumbwheel for use to adjust the distance between the lens assembly and the light emitting diodes. The distance between the lenses and the light emitting diodes may be adjustable by rotating a collar that moves the lenses.

In a twelfth aspect the invention provides an LED spot light having a plurality of LEDs emitting electromagnetic radiation. The spot light also has a lens associated with each LED so that the electromagnetic radiation passing through all lenses from their associated LEDs is substantially superimposed to a target area at a target distance from the lenses.

In a thirteenth aspect the invention provides a lens adaptor having a lens housing and lenses. The lens housing is for attachment to an LED spot light with a plurality of LEDs emitting electromagnetic radiation. The lenses are associated with each LED when the lens housing is attached to the spot light so that the radiation passing through all lenses from their associated LEDs is substantially superimposed to a target area at a target distance from the lenses.

In a fourteenth aspect the invention provides a lens and LED assembly. The assembly has a plurality of LEDs emitting electromagnetic radiation. The assembly also has a lens associated with each LED so that the electromagnetic radiation passing through all lenses from their associated LEDs is substantially superimposed to a target area at a target distance from the lenses.

The distance between the lenses and LEDs may be adjustable so as to permit changing the distance at which beam components formed by each light emitting diode and each associated lens are best focused.

The LED locations may be changeable to permit adjustment of the convergence angle formed by each lens/LED relationship to change the best focus distance.

The distance between lens centers may be smaller than the distance between the centers of their associated light emitting diodes so that the beam components formed by each lens from its associated light emitting diode converge towards each other.

The beam components may be formed by each lens from its associated light emitting diode converge towards each other so that all beam components coincide at a distance which can be changed by changing the distance between the lenses and the LEDs.

The distance between the lenses and the light emitting diodes may be adjustable so as to permit adjustment of the distance at which beam components are focused in addition to permitting adjustment of the distance at which beam elements are coinciding with each other. The distance between the lenses and the LEDs may be adjustable by means of a thumbwheel. The distance between the lenses and the LEDs may be adjustable by rotating a collar that changes the distance between the lenses with respect to the LEDs.

A sixth aspect of the invention is changing the focal length of the lenses to increase the size of the spot of light by decreasing the focal length of the lenses and the distance between the lenses and LEDs or to reduce the size of the spot of light by increasing the focal length of the lenses and the distance between the lenses and LEDs.

The distance separating the LEDs from each other may be adjustable along with the distance between the lenses and the LEDs. The distance separating the LEDs and the distance between the lenses and the LEDs may both be adjusted by the same adjustment. The lenses may be within and spaced about a single lens mount, and the LEDs may be mounted on a printed circuit board. An assembly may also have a spacer through which the LEDs project, the spacer for correctly spacing the LEDs with respect to one another for alignment with the lenses.

There may be a separator between the lenses and the LEDs, such that light from each LED cannot pass through the separator to a lens not associated with LED, and light from each LED can pass through the separator to the lens associated with that LED.

There may be a baffle that includes the spacer and the separator. The baffle and lens mount may be fixed to one another to limit relative movement of the baffle and the lens mount.

The printed circuit board may be held in fixed relationship to the lens mount, with a desired distance between the lenses and their associated LEDs. The lens mount may have a tubular body extending away from the lenses, and the baffle may fit within the tubular body until the separator meets the lens mount about the lenses.

The lens mount may have a tubular body extending away from the lenses, and the printed circuit board may be fixed to the tubular body.

Other aspects and embodiments of the invention are set out elsewhere herein, or will be evident to those skilled in the art based on the principles presented herein.

BRIEF DESCRIPTION OF THE DRAWINGS

For a better understanding of the present invention and to show more clearly how it may be carried into effect, reference will now be made, by way of example, to the accompanying drawings that show the preferred embodiment of the present invention and in which:

FIGS. 28 and 29 are ray diagrams that illustrate the increase and decrease of the image size as the lens focal length is decreased and increased.

PREFERRED EMBODIMENTS

In this description, the term "LED source" is used. Unless the context requires otherwise, an "LED source" encompasses a single LED or a plurality of LEDs. LEDs include superluminescent diodes or laser diodes as well as conventional and other light emitting diodes. Laser diodes used in inspection spot lights may be operated in a laser mode or in a non-laser mode.

Also, numerous variants are described. Again, unless the context requires otherwise, such variants apply equally to all of the alternative embodiments described herein.

Placing a convex lens forward of a light emitting diode can collimate the light from the light emitting diode into a beam which is narrower and better defined than the beams produced by light emitting diodes. Typically the lens would be forward from the LED by a distance approximately equal to the focal length of the lens so that the beam consists of an image of the front surface of the LED.

Several LEDs, each with a lens, produce beams that can be combined into one bright beam. A light head having several LEDs and associated lenses would be an LED spotlight with several applications. For example, the light head may be combined with suitable circuitry such that it can be powered by 120 or 230 volts AC so that it can be used as an accent light. The light head may be combined with resistors or current regulating circuitry such that it can be powered by batteries so that it can be used as part of a flashlight.

Figure 1:
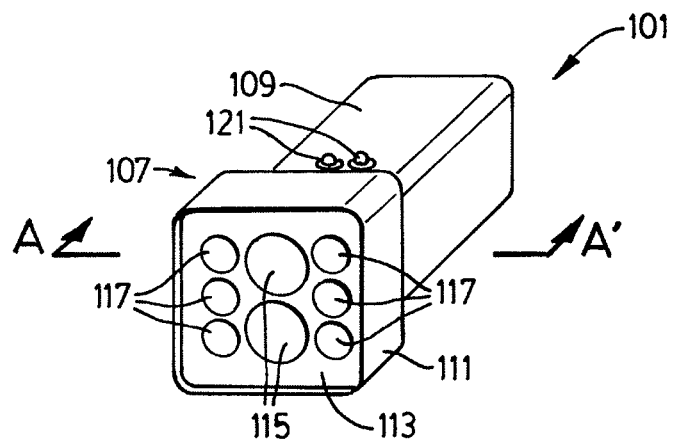
FIG. 1 is an external view showing the front, top, and left side of a light according to a preferred embodiment of the invention.
Figure 2:
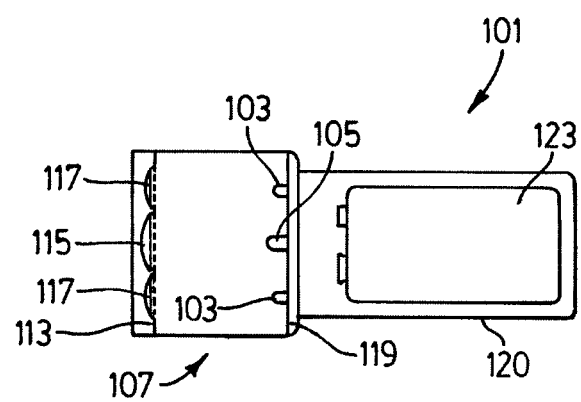
FIG. 2 is a cross sectional view through the line A-A', looking from above, of the light of FIG. 1.

Referring to FIG. 1 and FIG. 2 an inspection lamp 101 has six light emitting diodes 103 that produce ultraviolet radiation and two light emitting diodes 105 that produce blue visible light. The diodes are placed in a configuration similar to the lenses—later introduced as 115, 117—except as otherwise set out herein. The ultraviolet light emitting diodes 103 are of a currently available type having a peak emission wavelength of 370 nanometers with a narrow beam emission permitting the smaller lens. The blue light emitting diodes 105 may be of a preferred type having a peak emission wavelength of approximately 460 nanometers, or of a more easily available type having a peak emission wavelength of approximately 470 nanometers with a wider beam emission and therefore requiring the larger lens. The number of ultraviolet light emitting diodes 103 is greater than the number of blue light emitting diodes 105 because the output power of this type of ultraviolet light emitting diode 103 is typically low compared to that of high brightness blue light emitting diodes 105.

Light emitting diodes of types and quantity different from those described may be used as they are available.

The inspection lamp 101 resembles a flashlight by having a distinct "head" section 107 attached to a distinct handle section 109, with these two sections 107, 109 sharing a common longitudinal axis.

The "head" section 107 has a head casing 111 which contains a forward bulkhead or "lens board" 113 which several lenses (115 and 117) are attached to, and which also contains a rear bulkhead or "light emitting diode board" 119, which the light emitting diodes 103, 105 are attached to. The lens board 113 is mounted sufficiently rearward from the head casing 111 for the head casing 111 to protect the lenses 115, 117 from most accidental impacts.

The head casing 111 is attached to a handle section casing 120. These two casing sections 111, 120 may be considered a single part for manufacturing purposes. The casings shown in the Figures are only examples. As will be evident to those skilled in the art, many different shapes and sizes of cases may be used. Casing design may be based on such factors as size, shape, comfort, available components, power source used, cost and visual aesthetics.

Mounted to the lens board 113 are two larger lenses 115 used to concentrate the outputs of the two visible blue light emitting diodes 105. Also mounted to the lens board 113 are six smaller lenses 117 used to concentrate and superimpose the outputs of the six ultraviolet light emitting diodes 103 to a target area at a target distance from the lenses 117. In this embodiment, all lenses 115, 117 are of the plano-convex type, with their convex surfaces facing forward, and mounted approximately their own focal lengths forward from the most forward points of their associated light emitting diodes 103, 105. Other types of lenses, such as bi-convex, meniscus (concave-convex) with similar focal lengths may be used. The plano-convex lens may have advantages in manufacturing and low sphere-related distortions of lenses where the object distance and image distance from the lenses are unequal. An asymmetrical bi-convex or meniscus lens may provide the best distortion characteristics.

It has been found for all embodiments that the target area should be greater than 1 inch wide at a target distance selected from between 5 inches and 3 feet.

For most applications, the target area is limited by the intensity of the LEDs. If the LEDs are sufficiently intense then the beam can be concentrated to a larger target area. If the LEDs are relatively weak then the beam will need to be further concentrated to a smaller target area. For clarity, the beam does not have to fall with the target area for all target distances, only for at least one target distance that is useful for the particular desired leak detection application. For the particular configurations described in this application, it has been found that a target area of approximately 2 to 7 sq. inches provides usable intensity at a usable target distance of between 4 and 20 inches. More intense LEDs or more LEDs could provide a larger target area at a useful target distance. Lens 115, 117 mounting positions at different distances from their associated light emitting diodes 103, 105 may be favorable in use in some applications. Lens 115, 117 could be positioned at different positions forward of their associated light emitting diodes as an alternative embodiment.

The light emitting diode board 119 is mounted just forward of the rear surface of the head casing 111. Mounted to the light emitting diode board 119 are the two blue light emitting diodes 105 and the six ultraviolet light emitting diodes 103. Alternatively, the rear surface of the head casing 111 may be used as a surface to mount the light emitting diodes 103, 105 to, possibly eliminating the need for the light emitting diode board 119.

Two momentary contact switches 121 are incorporated into this embodiment, with one to be pressed to operate the blue light emitting diodes 105 and the other to be pressed for operation of the ultraviolet light emitting diodes 103. It is permissible to press both switches 121 should it be desirable to have all of the light emitting diodes 103, 105 operating. It is possible that the operator is unaware of which dye is being used, or that the visible light from the LEDs 105 may be useful for illuminating the site being viewed while ultraviolet reactive dyes are being used, or that the radiation from one set of LEDs, for example, 103 may contain a wavelength that the fluorescent dye reacts to, even if to a lesser extent than it reacts to the wavelengths emitted by other group of LEDs 105.

Figure 6:
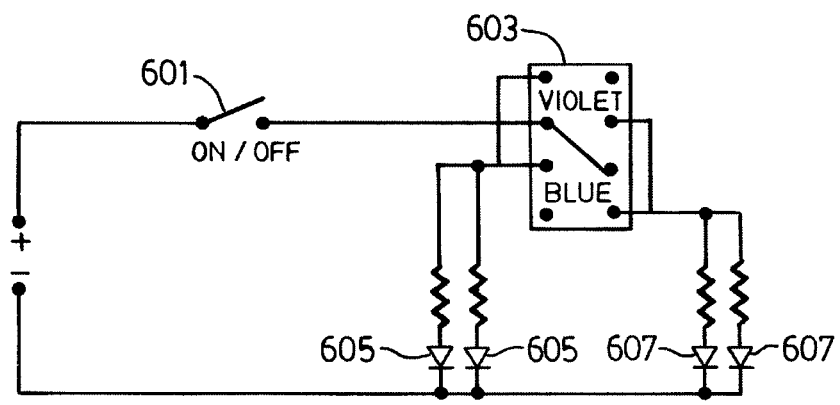
FIG. 6 is a schematic diagram of an example alternative electrical circuit for lights according to the preferred embodiments that have multiple LED sources.
Figure 7:
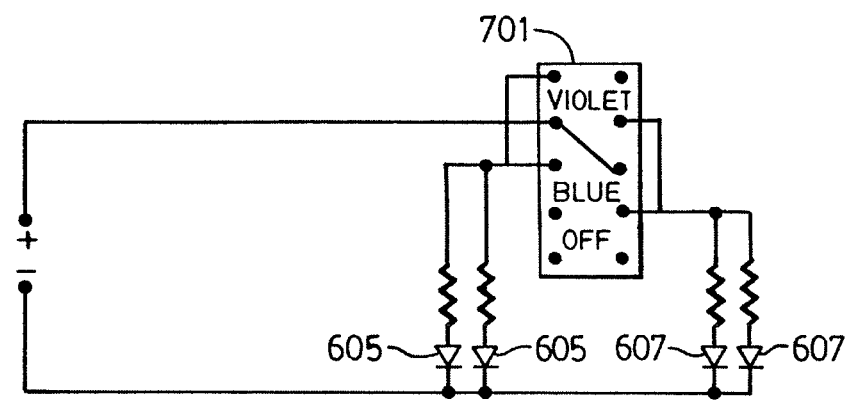
FIG. 7 is a schematic diagram of an example further alternative electrical circuit for lights according to the preferred embodiments that have multiple LED sources.

The light emitting diodes are powered by a battery 123 that the handle casing 119 is designed to accept. One terminal of the battery 123 would typically be connected to the cathode terminals of all of the light emitting diodes 103, 105. The other terminal of the battery 123 would typically be connected to one terminal of each of the momentary contact switches 121. The other terminal of each of these switches 121 typically connects to the anode terminals of their associated light emitting diodes 103, 109 through appropriate dropping resistors (not shown in FIG. 1 or FIG. 2; however, an examples for alternate embodiments are shown in FIG. 6 and FIG. 7). Batteries would produce direct current. In low energy and portable small size applications, small dry cell batteries may suffice. For higher energy consumption larger batteries of, for example 12 or 48 volts, may be more practical. In this case, the batteries may have to be external to the light.

There are several ways to properly limit the current flowing through the light emitting diodes 103, 105, including linear current regulator circuits (such as those shown in FIG. 6 and FIG. 7) and switching current regulator circuits. It is also possible to select battery types with sufficient internal resistance not to require dropping resistors or other current limiting means. Current limiting means such as dropping resistors would typically but not necessarily be mounted to the light emitting diode board 119.

Protection can be provided to accept reversed polarities, or to prevent reversed polarities from damaging the LEDs or other lamp components.

Variations of this or other embodiments may be designed to accept power from an external power source, such as an alternating current power source of, for example 120 or 230 volts AC.

A variation of this embodiment having no lenses or lenses for only some of the light emitting diodes may be useful with light emitting diodes having adequately narrow beam characteristics.

Figure 3:
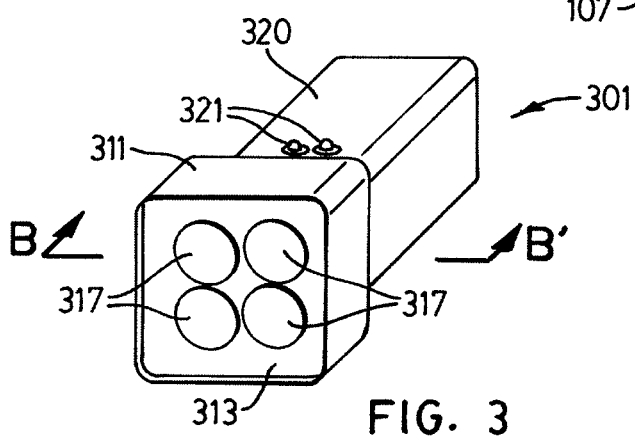
FIG. 3 is an external view showing the front, top and left side of a light according to an alternate preferred embodiment of the invention.
Figure 4:
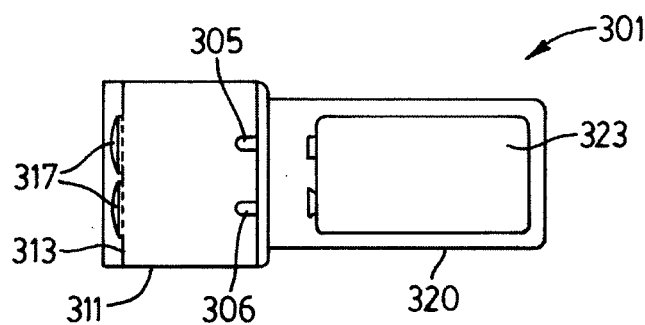
FIG. 4 is a cross sectional view through the line B-B', looking from above, of the light of FIG. 3.

Referring to FIG. 3 and FIG. 4 show an alternative inspection lamp 301 has two light emitting diodes 305 that produce blue visible light and two light emitting diodes 306 that produce violet visible light. Again, the LEDs each pair are lined up with one another in a similar manner to the later introduced lenses 317, except as otherwise set out herein. The blue light emitting diodes 305 are of a high output type having a peak emission wavelength in the range of 440 to 475 nanometers. The violet light emitting diodes 306 are of a high output type having a peak emission wavelength of approximately 405 nanometers. Alternatively, the shorter wavelength light emitting diodes 306 may be of an ultraviolet type having a peak emission wavelength of 395 nanometers or less while the longer wavelength light emitting diodes 305 would have a peak emission wavelength anywhere from 405 to 475 nanometers.

The lamp 301 resembles the lamp 101 by having a distinct head casing 311 and handle casing 320 sharing a common longitudinal axis so as to resemble a "flashlight". These two casing sections 311, 320 may be considered one part for manufacturing purposes. A forward bulkhead 313 or "lens board" has mounted to it four identical plano-convex lenses 317. These lenses 317 concentrate and superimpose the outputs of two blue light emitting diodes 305 and two violet light emitting diodes 306.

The blue and violet pairs of light emitting diodes 305, 306 can be activated by pressing associated momentary contact switches 321.

The handle casing section 319 accepts a battery 323 that is used to power the light emitting diodes 305, 306.

Again, current limiting means (not shown) may be dropping resistors or current regulation circuitry. Alternatively, the battery may be of a type having high enough internal resistance or other characteristics such that current regulation means is not necessary. Again, variations of this embodiment may be designed to accept power from an external power source.

Figure 5:
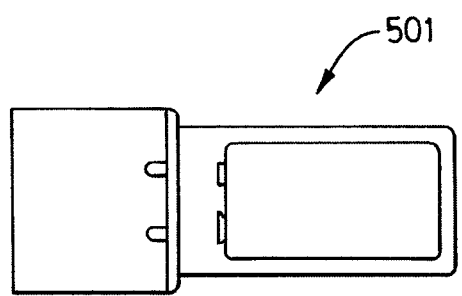
FIG. 5 is a cross sectional view looking from above of a light according to a further alternate preferred embodiment of the invention.

Referring to FIG. 5, a further alternate inspection lamp 501 does not use concentrating lenses, and is otherwise the same as lamp 301. In this case, the advantages of LEDs with different wavelengths are retained, and, provided the LEDs are of sufficient intensity, the resulting beam will continue to be usable in leak detection.

As intimated earlier, in any of the embodiments, it can be advantageous to utilize narrow beam LEDs. In this description a narrow beam LED is said to produce a concentrated beam. As indicated previously, a beam originating from near the focal plane of a lens will also result in a concentrated beam. When a concentrating lens is used in combination with a concentrated beam from an LED then more of the energy from the LED can be made to pass through the lens. It can be particularly useful to use a concentrated beam from an LED when a concentrating lens is not used. By directing more of the energy from the LED directly at the area to be viewed, the resulting fluorescence will be increased when compared to a wider beam from an equally powerful source. The beam area at the target site is selected to provide a useful target area for leak detection. If the beam area is too small then portions of the system being tested may be inadvertently missed. If the beam area is too great then the intensity of the radiation at the target site may be insufficient.

If it is desired to use a particularly narrow beam LED, or an LED that has over convergent internal optics then diverging lenses may be used to create a target area sufficiently large to be usable.

Many alternate embodiments are possible, including, for example, those having only one switch to control all light emitting diodes. As another example, Embodiments of this invention may have any switching means commonly used in flashlights, such as switching means where switching is accomplished by rotating the head section.

Another embodiment could include one very high power blue light emitting diode, such as a maximum current rating of 350 milliamps, along with several lower power light emitting diodes that produce visible violet light or ultraviolet radiation.

Both visible violet and ultraviolet light emitting diodes may be used in addition to the blue light emitting diode, such that light emitting diodes of more than two types are used.

Alternative configurations can include any number of light emitting diodes depending on the specifications and the desired application of the lamp. When using LEDs emitting significant radiation of the same wavelength as a fluorescent dye may emit, it can be desirable to have a switch or combination of switches (such as switches 121) that allow selection of individual LEDs or groups of LEDs.

Referring to FIG. 6 and FIG. 7, other alternative switch configurations may be used, for example, a momentary switch 601 can be used in combination with an LED selector switch 603. The LED selector switch 603 selects between either LEDs 605 or LEDs 607, or both. When the momentary switch 601 is activated the currently selected LEDs will be energized. A two-pole three position switch 601 is suitable where two groups of LEDs 605, 607 are used. As an alternative example, a single switch 701 can be used to perform both the selection and activation function. A two-pole four position switch 701 is suitable where two groups of LEDs 605, 607 are used.

The switches 603, 701 are 2-pole multi-position slide switches. The switch diagrams show only the fixed contacts within the switches 603, 701. The moving part of each switch 603, 701 (not shown as is often done in a slide switch wiring diagram), within the left column and repeated in the right column, connects two vertically adjacent contacts.

Figure 8:
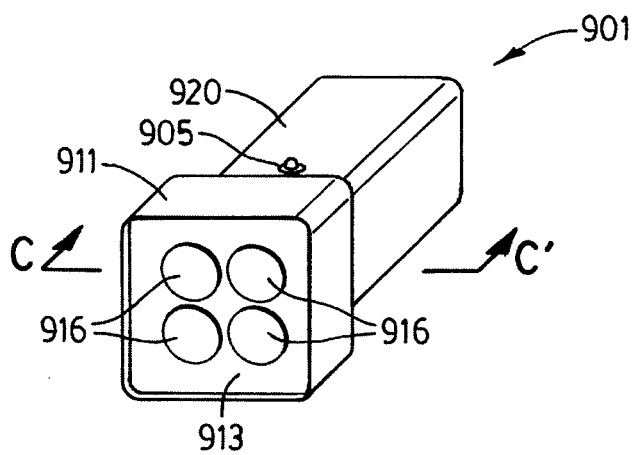
FIG. 8 is an external view showing the front, top, and left side of a light according to a further alternate preferred embodiment of the invention.
Figure 9:
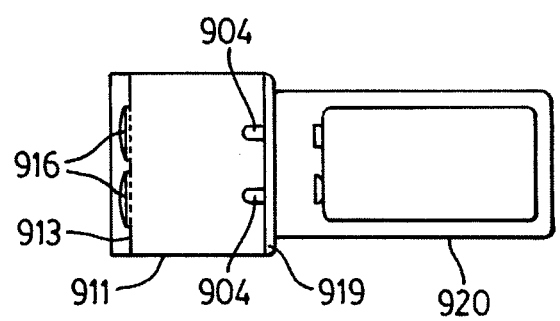
FIG. 9 is a cross sectional view through the line C-C', looking from above, of the light of FIG. 8.

Referring to FIG. 8 and FIG. 9 an inspection lamp 901 has four light emitting diodes 904 having a peak wavelength of anywhere from 370 to 475 nanometers. The light emitting diodes 904 may have significantly different peak wavelengths so as to excite a variety of fluorescent materials. The lamp has a single switch 905, and is otherwise similarly configured to the lamps 101, 301, with a distinct head casing 911 and handle casing 920. A forward bulkhead 913 or "lens board" has mounted to it four identical plano-convex lenses 916. These lenses 916 concentrate and superimpose the outputs of the light emitting diodes 904.

It may be important to note that in some circumstances, particularly if there is sufficient intensity, wavelengths below 395 nanometers may be harmful. Safety precautions may be necessary.

Figure 10:
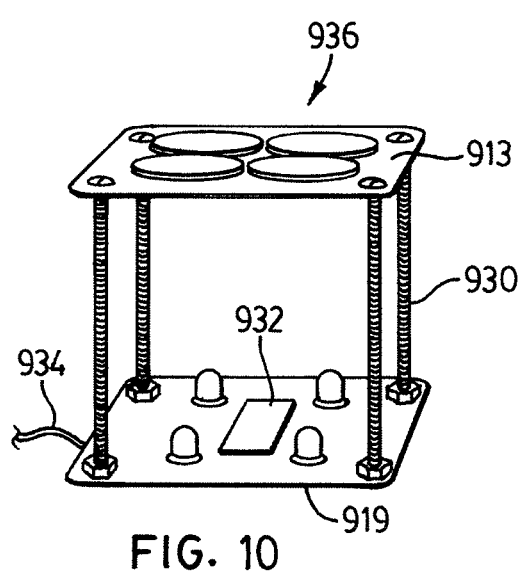
FIG. 10 is an external view showing the front, top, and left side of a lens/LED assembly according to a preferred embodiment of the invention.

Referring to FIG. 10, as an example, a lens board 913 and a LED board 919 are maintained in fixed position with respect to one another by spacers 930. Current limiting circuitry 932 is also contained on the board 919 and wire 934 is provided for connection to a battery, not shown. The other connection to the battery is by way of a button contact on the underside of the board 919. The lens board 913 and LED board 919 form lens/LED assembly 936.

A lens/LED assembly, such as the assembly 936 can replace the reflector and/or the bulb of an ordinary flashlight, not shown, in order to convert the flashlight to an inspection lamp suitable for selection of fluorescent materials. The dimensions of the assembly 936 may need to be altered in order to fit within the flashlight. For example, many flashlights are round; so, the shape of the boards 913, 919 could be made circular. All such modifications fall within the spirit and scope of the invention, the preferred embodiments of which are described herein.

In the presently preferred embodiments of the invention, the lenses are forward of the tips of the light emitting diodes. The distance from the tips of the light emitting diodes is slightly greater than the focal length of the lenses, such that each lens forms a distinct circular image of the light emitting diode at a distinct distance forward from the lenses. The centers of the lenses are separated from each other by a distance slightly less than the distance between the centers of the light emitting diodes, such that lines from the centers of each of the light emitting diodes through the centers of their associated lenses converge at the same distance forward from the lenses that the forward portions of the bodies of the light emitting diodes are focused.

Alternatively, the lenses may be placed forward from the light emitting diodes at a distance from the tips of the light emitting diodes to the lenses that is approximately the focal length of these lenses so as to produce a smaller and more intense spot at the point of convergence.

Figure 11:
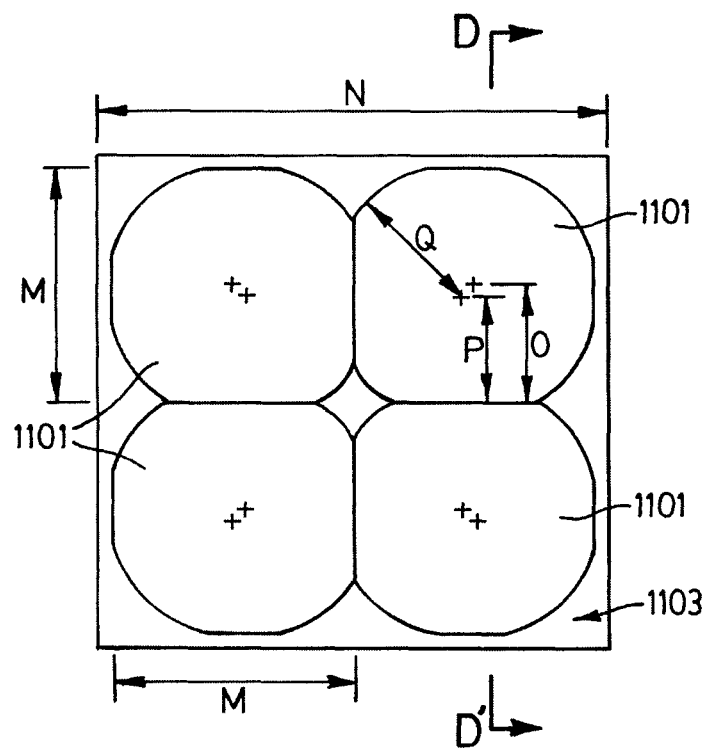
FIG. 11 is a frontal view of a lens assembly according to a preferred embodiment of the invention.
Figure 12:
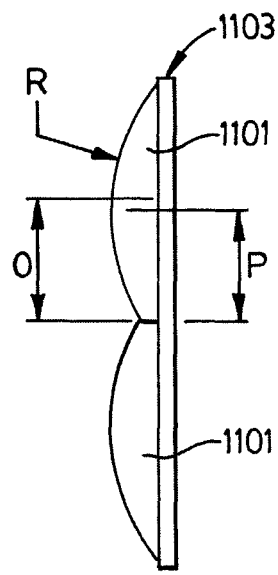
FIG. 12 is a side cross sectional view through the line D-D' of the lens assembly of FIG. 11.

Referring to FIG. 11 and FIG. 12, lenses 1101 may be formed in a lens assembly 1103 from a single moulded piece of suitable transparent material. The lenses 1101 in lens assembly 1103 are in the shape of squares with rounded corners to reduce the spacing between their centers compared to circular lenses having the same area.

Each of lenses 1101 may have its principal point displaced to one side of the center of its area so as to have some prism character. This would be done to form beams whose axes intersect at some specific distance forward of the lens assembly if each emitting diode is centered to the rear of the center of the area of each lens and the axis of each light emitting diode passes through the center of the area of each lens.

It is recognized that in any of the embodiments described herein, there may be radiation from an LED that passes through a lens other than the lens with which the LED is associated. This can result in secondary images of the LED, typically spaced around and separate from the superimposed images. Although it may be aesthetically distracting, this effect will not be detrimental to the use of the lamp. There are a number of ways to avoid this "cross-talk" between LEDs and non-associated lenses. For example, concentrated beams from LEDs could be used or separators could be placed between the LEDs so that non-associated lenses cannot "see" other LEDs.

Referring again to FIGS. 11 and 12, in the preferred embodiment of the lens assembly 1103 width M of a lens 1101 is 13 mm, the overall width N of the lens assembly 1103 is 27.4 mm, the distance 0 from the centerline of the lens assembly 1103 to center between edges of each lens 1101 is 6.5 mm, the distance P from the centerline of lens assembly 1103 to center of curvature of each lens 1101 is 6 mm, the radius Q is 7.2 mm, and the radius of curvature R of each lens assuming a refractive index of 1.5 is 11.1 mm. Those skilled in the art will recognize that other combinations of parameters can be used in accordance with the principles described herein.

Figure 13:
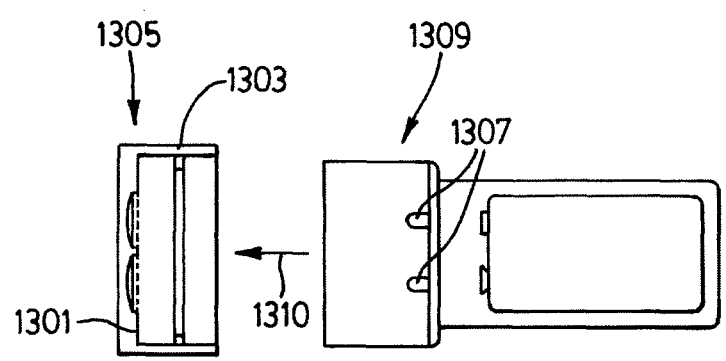
FIG. 13 is a cross-section view of a lens adapter according to a preferred embodiment of the invention in use with a multiple LED inspection light.

Another embodiment could be a lens assembly to be added to an existing flashlight having multiple light emitting diodes suitable for causing visible fluorescence of fluorescent materials. Referring to FIG. 13, the lens assembly 1301 could be contained in a housing 1303 to form a lens adapter 1305. In the preferred embodiment, the adapter 1305 is formed from a resilient material such as rubber, and the adapter 1305 slips over the head of an existing multiple LED 1307 lamp 1309 (as indicated by arrow 1310). The adapter 1305 has stops 1309 to assist in positioning the adapter 1305 to properly place the lens assembly 1301 in relation to the LEDs 1307. Different adapters 1305 will likely be necessary to match the particular configuration of each lamp 1309. Alternate means for removably attaching the adapter 1305 to lamp 1309 will be evident to the those skilled in the area, including, for example, a tight fitting stiff plastic for a manual fit.

Referring to FIGS. 14-18, further details of possible relationships between the lenses and LEDs will now be discussed.

Figure 14:
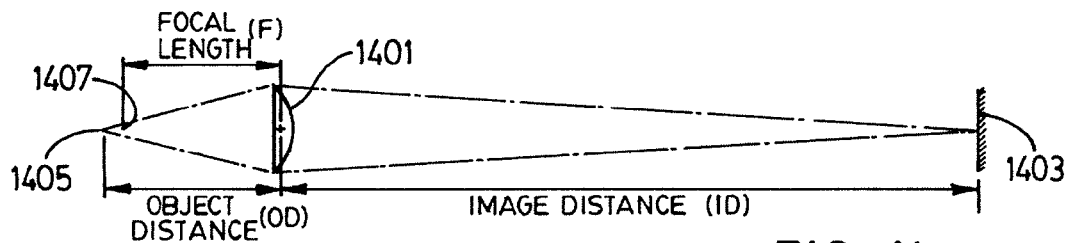
FIGS. 14-18 are ray diagram of illustrating some of the factors utilized in the preferred embodiments of the invention.

Referring to FIG. 14, a convergent lens 1401 can form an image 1403 of an object 1405. If the object 1405 is at the focal point 1407 of the lens 1401 (on one side of the lens), or at a distance (OD) from the lens 1401 equal to the focal length (F) of the lens 1401, then an image 1403 is formed at the other side of the lens 1401 at infinite distance (ID) from the lens 1401. By movement or focus of the lens 1401, the image 1403 is well-enough formed at all far distances and at any point beyond this distance the image is larger and blurred or out of focus.

There is a relationship among object 1403 distance (from the lens 1401), image distance (ID) (from the lens 1401), and focal length (F) of the lens 1401: 1l object distance+1 image distance=1 focal length In the lamp 901, the lenses 916 have a focal length of 35 mm, and they are placed 40 mm from the LEDs 904 (by theory) to produce a focussed image of the front surfaces of the LEDs 904 at 280 mm from the lenses 916.

Each lens of a multi-lens multi-LED flashlight, embodiments of which are described herein, makes good use of only the one LED with which it is associated. Each LED-lens combination concentrates the beam from the LED to form a "spotlight". These "spotlights" operate optically independent of each other but are aimed onto a common target and thus "superimposed"—in the case of lamp 901, 280 mm forward of the lenses was chosen as the common target distance from the lenses.

Figure 15:
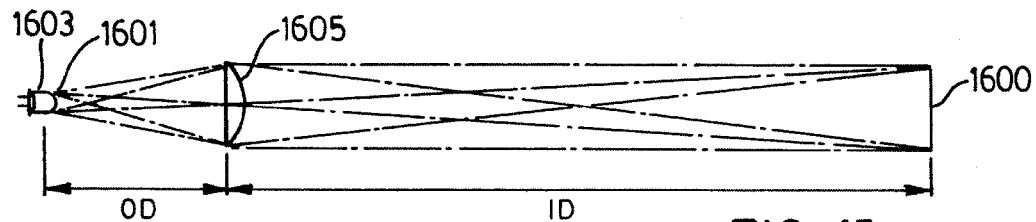

Referring to FIG. 15 ray paths involved in formation of an image 1600 of the front surface 1601 of an LED 1603 are shown. The LED 1603 is separated from lens 1605 by a distance slightly greater than the focal length of the lens 1605 and the image 1600 is formed at some distinct distance from the lens 1605. The image 1600 of the front surface 1601 of the LED 1603 is an attractive bright circle, assuming that all portions of the front surface 1601 of the LED 1603 are passing rays utilized by the lens 1605. The lamp 901 has four independent LED-lens combinations, each form a circular image onto the same area at a design "target distance" of 280 mm from the lenses 916.

Figure 16:
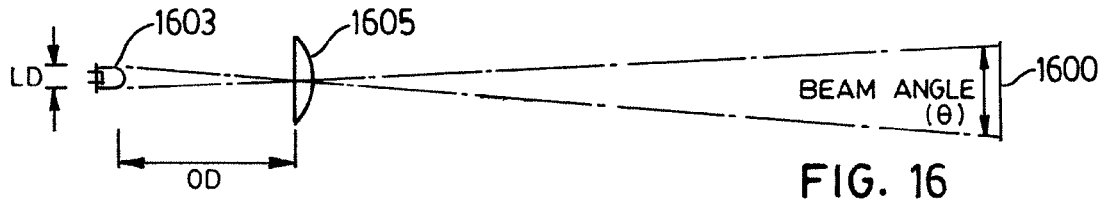

Referring to FIG. 16, rays from the edges of the LED 1603 are shown passing through the center of the lens 1605 to the edges of the image 1600, to illustrate the beam angle as a function of LED diameter (LD) and the distance (OD) from the LED 1603 to the lens 1605. Theoretically exactly, the tangent of half the beam angular diameter is equal to the ratio of LED radius (½ LD) to its distance (OD) from the lens 1605. As a useful approximation, the beam diameter in radians will usually be the ratio of LED diameter (LD) to the distance (OD) from the LED 1603 to the lens 1605. Multiplying this figure by 57.3 gives an approximate beam angular diameter in degrees.

Flashlights have a typical beam diameter of only a few degrees while many of the latest high output LEDs have a typical beam diameter of nominally 15 degrees. It has been found that a beam angular diameter less than 15 degrees is desirable for a flashlight-like sort of inspection lamp. A beam diameter of 7-8 degrees produces a spot width of about 1.5 inches at 1 foot.

In the lamp 901, the LED diameter is 5 mm and the LEDs are approx. 40 mm from the centers of the lenses. Twice the arctangent of (half of 5/40) is approx. 7.2 degrees. Thus, the beam has an angular diameter close to this where it is best-defined (best-focused and converged) approx. 280 mm from the lenses of the lamp 901.

Figure 17:
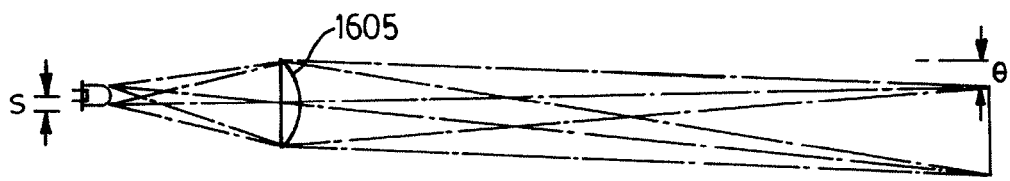

Referring to FIG. 17, shifting the LED 1603 slightly to one side (S) of the axis of the lens 1605 causes the resulting beam to form at a slight angle from the axis of the lens 1605. In the preferred embodiment of the lamp 901, the four lenses 916 are centered approx. 17.5 mm from each other vertically and horizontally, or 8.75 mm from the lens assembly's common axis vertically and horizontally.

The beams projected from each lens 916 converge onto each other at 280 mm from the lenses 916, so their centerlines deviate from the centerline of the lamp 901 so as to shift 8.75 mm vertically and horizontally from the lens axes per 280 mm of distance forward of the lenses 916.

To achieve this, the LEDs 904 are mounted in positions displaced outward from the lens axes both horizontally and vertically by (8.75*40/280) mm from the lens axes, or 1.25 mm both vertically and horizontally from the lens axes, or approx. 1.77 mm from the axes of their associated lenses 916 on lines passing through the lens assembly center, the lens axes, and the LEDs 904.

To achieve this for the preferred embodiment, the LEDs 904 are mounted in positions displaced outward from the lens 1605 axes both horizontally and vertically by (8.75*40/280) mm from the lens assembly axis or 1.25 mm both vertically and horizontally from the axes of their associated lenses 916, or approx. 1.77 mm total diagonal distance from the axes of their associated lenses 916.

Figure 18:
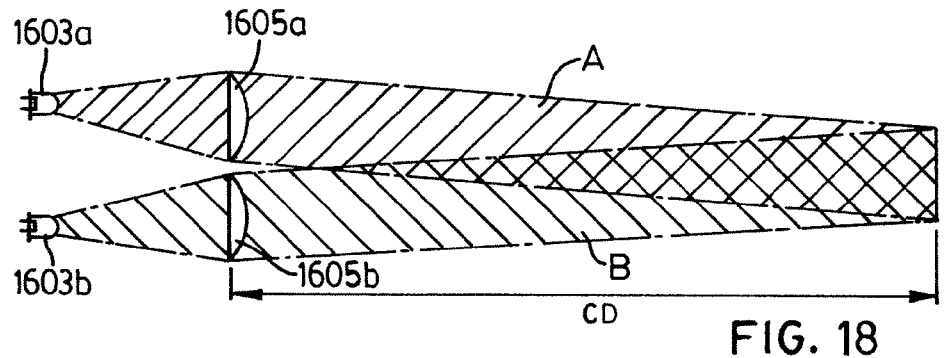

Referring to FIG. 18, two LED-lens combinations 1605a/1603a, 1605b/1603b with LEDs offset from the axes of their associated lenses produce two beams A, B that coincide at a specific distance (CD) from the lenses 1605. Not shown in FIG. 18 is rays explaining how the beams are best-defined at the same distance. However, design of a flashlight having multiple "independent units" each consisting of an LED 1603 and a lens 1605 would preferably have the beams best-defined (focused images of the front surfaces of the LEDs) at the same distance at which their centerlines intersect.

Although it is not strictly necessary to have a focused image, it minimizes light wasted into a less illuminated "blur zone". Another advantage of a beam with sharp edges is that a sharp beam edge makes it easier to determine whether or not an area being inspected is being illuminated by the beam.

The above explains how a multi-lens multi-LED flashlight produces a beam that is attractive and impressive at a specific distance from the lenses. It is desirable to have as wide a range of useful "working distance" as possible.

Generally, a shorter lens focal length compared to the "typical working distance" or "design working distance" results in the beams being well-defined over a wider range of distances. However, a shorter focal length results in a wider beam. This can be countered by use of smaller diameter LEDs to the extent such smaller LEDs are available. The "usual size" of LED is 5 mm (often known in the USA as "T13/4"), with the next-most-common size being 3 mm (often known in the USA as Another consideration is that the smaller the lens area required to utilize the beam is, the less the beam loses definition at distances other than the target area. Smaller size LEDs lose most of their advantage here, since they are generally not available in beam width as narrow as that of narrow beam versions of larger LEDs. The main effect of the relationship between LED size and narrowest available beamwidth is to largely set a preferred minimum lens diameter of approx. 13 mm to produce a roughly 7-8 degree beam.

However, the shorter focal length of lenses to be used with smaller diameter LEDs is advantageous in having individual beams from each lens retaining good definition over a wider range of distances—to the extent that suitable LEDs are available in the smaller size.

One more consideration is making the lines passing through the center of the LEDs and the "principal point" of its associated lens to have the least possible angle of convergence. This makes the beams largely coincide with each other over a larger range of distances. One way to make the beam axes have a reduced angle of convergence is to use smaller diameter lenses.

However, the lenses must be large enough to catch most of the output beams of the LEDs. Narrower beam LEDs are advantageous here.

It should be noted that most 5 mm LEDs have significant light output to 7.5-8 degrees from the LED axis, or in other words have a 15-16 degree beam. 5 mm LEDs with substantially narrower beamwidth have significant output outside their nominal beam area, often as a "secondary ring beam" 15-18 degrees in angular diameter. 3 mm LEDs have nearly proportionately wider beams, and permit only a small reduction in lens diameter.

One more consideration is that the angular diameter of each beam exiting a lens should exceed the angle between axes of the beams. Achieving this assures that all individual beams merge into each other at least partially for all distances from about half the "design target distance" to infinite distance.

The angle between beam centers, in degrees, is approximately 57.3 times the ratio of lens spacing (between centers of lenses in opposite corners of the lens assembly) to design target distance from the lens. This figure for the preferred embodiment of lamp 901 is 57.3 times (25/280) or approx. 5.1 degrees. Since this figure is less than the approx. 7.2 degree diameter of the individual beams, there is some area covered by all beams at all distances greater than the design target distance. If this is true, then generally it is also true that all distances as short as approx. half the design target distance can be illuminated by all of the individual beams.

As noted above with respect to FIG. 18, usual convex lenses 1605 in a usual configuration require the LEDs 1603 to be offset vertically and horizontally from the axes of the lenses 1605. A disadvantage of this is that the LEDs 1603 must be slightly tilted to be aimed at the centers of the lenses 1605 (which is done in the lamp 901) or the lenses 1605 must be large enough to capture "off-center" LED beams.

If the lenses 1605 have a "prismatic effect" of bending a ray passing through the center of the area of the lens, then the LED 1603 can be mounted directly behind the lens 1605 with the LED 1603 and lens 1605 having a common axis parallel to that of an inspection lamp. The lens 1605 would then form a beam which exits the lens 1605 at an angle from the axis of the lens 1605.

One way to achieve this is to use a plano-convex lens having the center of curvature offset slightly from a "centerline" parallel to the axis of the entire "flashlight unit" and passing through the center of the area of the lens. One possible arrangement is that each lens is 16.8 mm wide and the LEDs coincide with lens axis/centerlines 16.8 mm apart but the centers of the curvature of the curved lens surfaces are only 14.7 mm apart.

LEDs 40 mm from such lens elements would form beams bent after exiting from these lens elements so as to coincide with each other 280 mm from the lenses.

Referring to FIG. 12, one can see how the center of curvature of each lens 1101 is offset slightly from the center of the area of the lens 1101.

As otherwise described herein, a lens specification in an inspection lamp having a lens forward of each LED can be determined as follows:

1. For a given target distance and beam width of a design, the LED's distance from the lens would be the LED's diameter times the ratio of target distance to beam width at the target distance.

2. The lens focal length should be: 1/(1/(target distance from lens)+1/(LED distance from lens))

3. A lens should be barely wide enough to capture the beam produced by its LED.

Multiply the LED's distance from the lens by twice the tangent of half the beam angle, and add to this the LED's diameter. (Or determine experimentally how wide a lens is required to capture the LED's beam at the distance from the LED that the lens is to be located at.)

Most 5 mm narrow beam LEDs have a beam width, including any significant secondary beam features, of approx. 15-18 degrees. Most 3 mm narrow beam LEDs have an overall beamwidth of approx. 25-28 degrees. These are the presently preferred LEDs.

4. Then comes the offset between LED axis and lens axis to make the beams converge:

a) In the prototype shown in FIG. 10, ordinary convex lenses (with optical center coinciding with the center of the area of each lens) are used and the centers of the LEDs are spaced slightly further apart than the centers of the lenses such that rays from the lens centers pass through the lens centers unbent and converge upon the center of the target area. The LEDs would be angled to aim them at the lens centers.

b) A variation of this embodiment would have the lens centers closer together than the LED centers, but the LEDs are not aimed at the lens centers. The lenses would then need to be wide enough to capture the beams from the LEDs. This means that the lens radius needs to exceed the beam radius by the offset between the LED's axis and the axis of the lens in order for the lens to capture the beam.

c) Lenses with optical center offset from the midpoint of the lens can be used. Each LED can be directly behind the midpoint of the lens, but the optical center (center of curvature of curved surfaces) is offset from the midpoint of the lens (or lens element) so that a ray passing through the midpoint of the lens is bent. FIG. 12 shows a molded assembly of such lens elements.

Figure 19:
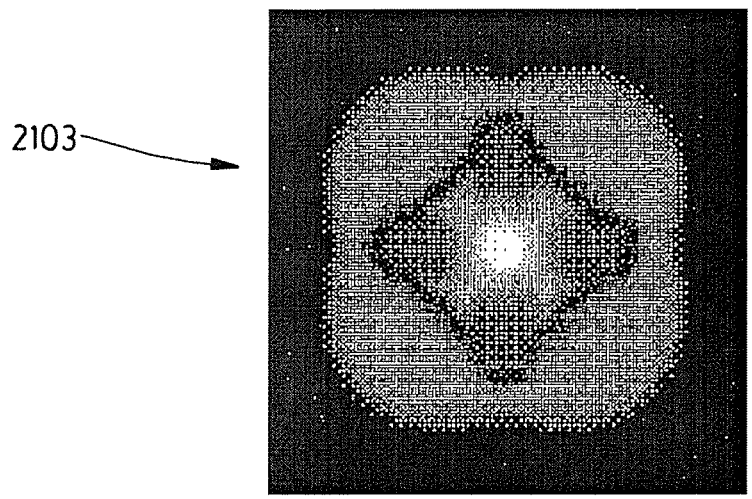
FIG. 19 is an image of the light of FIG. 8 at 6 inches.
Figure 20:
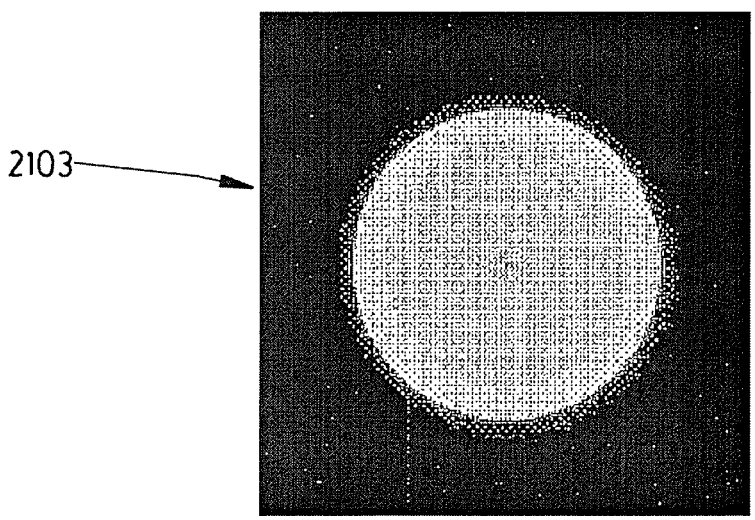
FIG. 20 is an image of the light of FIG. 8 at 11 inches.
Figure 21:
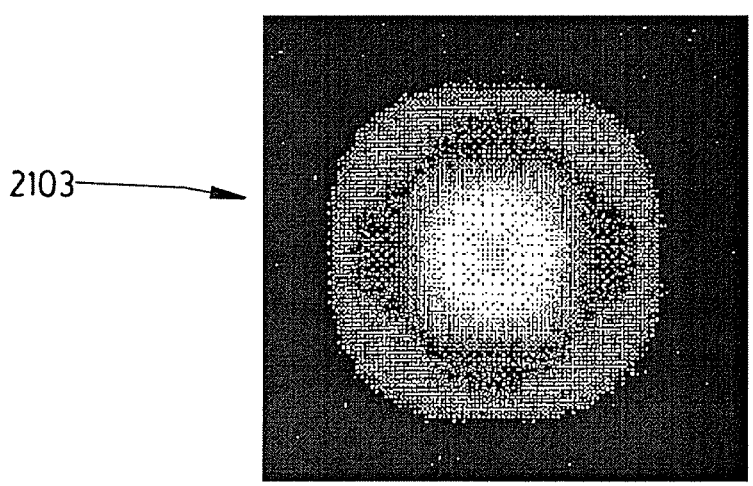
FIG. 21 is an image of the light of FIG. 8 at 20 inches.

Referring to FIGS. 19-21, the benefits of concentrating and superimposing lenses can be seen. Referring to FIG. 19, at a target distance of 6 inches a beam 2103 formed with lamp 901 is concentrated and partially superimposed.

Referring to FIG. 20, at 11 inches, the beam 2103 is well-defined (focused, concentrated and superimposed) in a given area. At this distance, the beam width was approximately 36 mm.

Referring to FIG. 21, at 20 inches the beam 2103 remains concentrated in a limited area. Although the beam is substantially superimposed, convergence is not perfect at this distance. Beam divergence spreads the beam to an ever increasing area which reduces the beam intensity.

Figure 22:
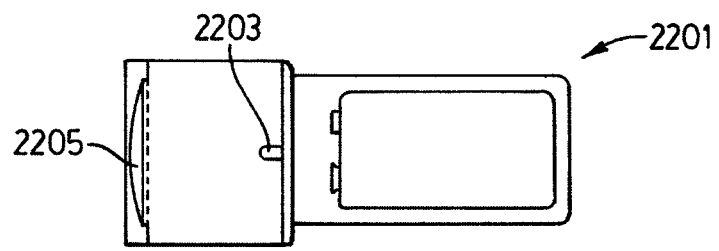
FIG. 22 is a cross sectional view looking from above of a light according to a further alternate preferred embodiment of the invention.

Referring to FIG. 22, a light 2201 has a single LED 2203 and a single converging lens 2205. The LED 2203 has a peak wavelength that is useful with a leak detection fluorescent dye, for example any of the LEDs previously mentioned could be used. The LED 2203 and lens 2205 combination is configured similarly to any one of the LED and associated lens combinations described previously; however, it is not necessary to offset the LED 2203 from the axis of the lens 2205, or to offset the principle point of the lens 2205, as the beam does not need to be superimposed on other beams. The light 2201 provides a more intense, concentrated beam than a single LED 2203 without such a lens. The light 2201 can be more compact than if multiple LEDs and lenses are used. The light 2201 can have useful battery life operating from a single "watch" type of battery.

For LEDs having particularly wide beams it is desirable to use the shortest possible focal length lens such as a plastic fresnel or pair of simple lenses. Some high power LEDs, for example 350 milliamps, are only available in wide beam angle, for example approximately 100 degrees. In a preferred embodiment of this configuration the diameter of the lens should approximate the focal length of the lens.

LEDs typically have a rated operating life of approximately 100,000 hours.

Leak detection lamps are typically operated sporadically for relatively short periods. All embodiments can be configured to drive LEDs at a greater wattage then their rated wattage ("overdrive"). This will reduce the lifetime of the LEDs, but will increase the intensity of the emitted radiation.

It may be appropriate to allow the lenses in a LED inspection light to be movable. For example, moving or focusing a lens assembly will permit some adjustment of beam convergence. The amount of adjustment in a multiple lens assembly may be limited since reduction of the distance from the LEDs and the lens assembly may eventually cause the lenses not to capture all of the light from each LED. As a further example, adjusting the distance between the LEDs and the lenses can adjust the distance at which the beams are in focus.

It is also possible to create inspection lights with multiple LEDs where only some of the LEDs have lenses. The LEDs not associated with lenses should be separated from LEDs associated with lenses by a sufficiently large distance (typically at least a lens diameter) so that lenses do not block the beams of LEDs that do not have lenses in front of them.

Alternative embodiments for use in generating visible light will now be described. As stated previously, the features and characteristics of the alternative visible light embodiments may be applied to the previously described embodiments, as desired.

Figure 23:
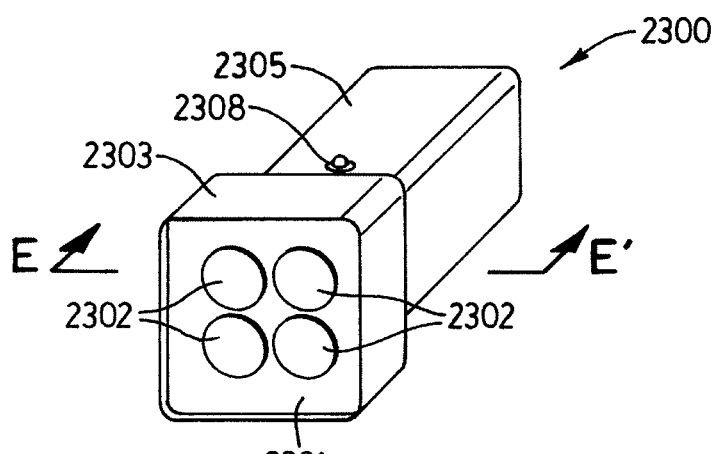
FIG. 23 is an external view showing the front, top, and left side of a light according to another further alternate preferred embodiment of the invention.
Figure 24:
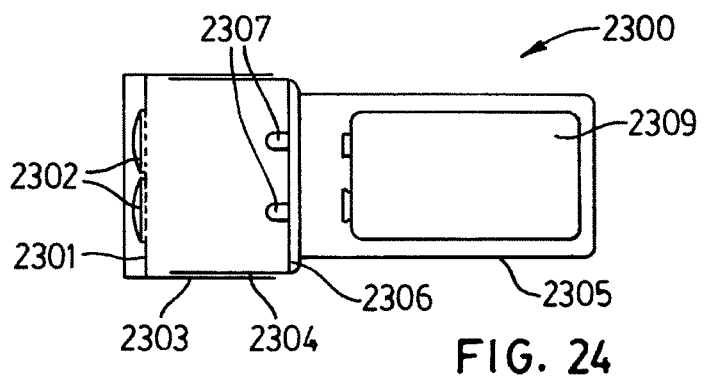
FIG. 24 is a cross sectional view through the line E-E', looking from above, of the light of FIG. 23.

Referring to FIGS. 23 and 24, a spot light in the form of a visible light flashlight 2300 is similar in layout to the lamp 901 of FIGS. 8 and 9. LEDs 2307 are mounted onto an LED board 2306, which is either mounted to or an integral part of the inner head casing 2304. The inner head casing is attached to a handle casing 2305. The inner head casing and the handle casing may be comprised in one piece for manufacturing purposes.

An outer head casing 2303 fits over the inner head casing. The outer head casing 2303 has a lens board 2301 mounted within it. The lens board 2301 has lenses 2302 to collimate (substantially superimpose to a target area at a target distance from the lenses) the light from the LEDs 2307 into beams narrower and better defined than the LEDs produce without lenses.

The LEDs 2307 are powered by a battery 2309. The LEDs 2307 typically require current limiting means (not shown), although it may be possible to produce the invention with batteries having internal resistance high enough to avoid the need for current limiting. The LEDs 2307 would typically be controlled by a switch 2308 that may be of the momentary contact pushbutton variety. The switch may be of another variety such as a slide switch or a push-on/push-off pushbutton.

The outer head casing slides over the inner head casing. This provides means to adjust the distance between the LEDs 2307 and the lenses to adjust the width and degree of concentration of the beam. This also provides means to make the beam best-focused at different distances from the flashlight.

The LEDs 2307 in this embodiment and other embodiments of the present invention may all be white LEDs 2307 or they may be colored LEDs 2307 selected to have their outputs combine to form light which is acceptable as white light.

An embodiment having colored LEDs 2307 can have one blue LED 2307a, one green LED 2307b, and two red LEDs 2307c. It is often found that when combining red, green and blue LEDs 2307 to produce white light, the number of red LEDs 2307c must exceed the number of green LEDs 2307a and the number of blue LEDs 2307b since red LEDs 2307c are often not as efficient in producing red visual response as green and blue LEDs 2307a,b are in producing their respective green and blue visual responses.

Use of red, green and blue LEDs 2307 can have an advantage over white LEDs 2307 for three reasons:

LEDs 2307 have a tendency to specialize in producing light in a specific region of the spectrum. White LEDs 2307 are typically blue LEDs having a phosphor added to them to convert some of the blue light to a band of wavelengths from green to red. Due mostly to the losses in the phosphor, white LEDs 2307 are less efficient than non-white LEDs 2307.

If a combination of red, green and blue LEDs 2307 is used, the spectrum of the combined output of the LEDs 2307 has more red and green content and less yellow content than is present in the spectrum of white LEDs 2307. The greater red and green spectral content increases the illumination of red and green objects. Yellow objects in general are illuminated by a combination of red and green light as effectively as they are by yellow light. A flashlight 2300 having spectral content richer than usual in red and green wavelengths at the expense of yellow wavelengths will illuminate red and green objects more brightly than usual for the given total light intensity, with minimal compromise in ability to illuminate objects of other colors such as yellow. This may be a useful characteristic of embodiments of the present invention that are used as flashlights or as accent lights.

The green LEDs 2307a can produce light mostly at wavelengths close to 507 nanometers, which is the wavelength at which night vision works best. A flashlight 2300 rich in wavelengths near 520 nanometers can work better for night vision than a flashlight 2300 with white LEDs 2307 which produce less light at wavelengths near 500-520 nanometers.

Combinations of colored LEDs 2307 other than red, green and blue can be used to produce white light and can be used in embodiments of the invention, although the ability to illuminate colored objects would generally be less than that obtained by using red, green and blue LEDs 2307. For example, blue and yellow LEDs 2307 can be combined to produce light that appears white. Likewise, red and blue-green can be combined to produce light that appears white. In addition, more than two different colors can be used and they could be other than red, green and blue. For example, light that appears white can be obtained by combining appropriate quantities of blue, green, and any color from red to orangeish yellow. Other examples to produce essentially white light include LEDs of yellow, green and blue, or yellow, turquoise and magenta. Flashlights 2300 producing a color other than white may be found to be desirable. Specifically, flashlights 2300 producing essentially yellow light may be found to be desirable. The LEDs 2307 in such a yellow flashlight may all be yellow or they may be green and red to achieve brighter illumination of red and green objects than is possible with a flashlight using yellow LEDs 2307. Various embodiments of a yellow version of the present invention may have orange and green LEDs 2307, or may have yellow LEDs 2307 combined with other colors that can be combined to result in essentially yellow light.

Combinations of colored LEDs 2307 may be selected to achieve high spectral content in green, blue-green and blue wavelengths favorable to scotopic vision (night vision). Such combinations are not limited to combinations that produce white light.

The LEDs 2307 may be mounted with their centers directly behind their associated lenses 2302 so that the beams formed by the lenses 2302 are parallel and merge into each other best at long distances from the flashlight 2300. Alternatively, the LEDs 2307 may be mounted with centers slightly further apart than their corresponding lenses 2302 are so as to make the beams produced by each LED 2307 converge at some specific finite distance forward of the flashlight 2300.

Lenses 2302 with their optical centers displaced from the midpoints between their edges can be used. This permits mounting the LEDs 2307 directly rearward of the midpoints between the edges of their associated lenses 2302 and achieving beams which are non-parallel such that the beams converge upon each other at a finite distance forward of the lenses 2302. The lenses 2302 may be part of a one-piece molded lens assembly 2301. The lenses 2302 would have a focal length large enough compared to the LED 2307 diameter to produce an adequately narrow beam. The beam formed by each of the lenses 2302 would have a width in radians approximately equal to the ratio of LED 2307 diameter to the focal length of the lens 2302 when the beam is best focused. Best focus of the beam is typically achieved by having the distance between the lenses 2302 and their associated LEDs 2307 approximately equal to the focal length of the lenses 2302 so as to form images of the front surfaces of the LEDs 2307.

The lenses 2302 would normally be as small as possible while large enough to capture the beams produced by their associated LEDs 2307. The minimum lens 2302 diameter for utilizing most of the light from the LEDs 2307 would be, approximately, the LED 2307 diameter plus the focal length times the width of the beams produced by the LEDs 2307 in steradians. LEDs 2307 of the narrowest available beam width would normally be selected to minimize the required size of the lenses 2302. LEDs 2307 may have alternate beam widths and lenses 2302 of alternate sizes.

In presently preferred embodiments of the invention, the lenses 2302 have a width of 14 mm and a focal length of 24-25 mm and the LEDs 2307 are 3 mm in diameter and have a beam width of approximately 25 degrees. This results in a beam approximately 3/24 or 1/8 steradian wide, or approximately 7 degrees wide. A beam of such width can be achieved using 5 mm LEDs 2307 with a beam width of approximately 15 degrees and lenses 2302 with a width of 16 millimeters and a focal length of 40 millimeters.

Movement of the lenses 2302 with respect to the LEDs 2307 may be useful to adjust the width and degree of focus of the beam produced by the flashlight 2300, or to make the beam as narrow and/or as focused as possible at a specific distance from the flashlight 2300.

Flashlight 2300 has four LEDs 2307 and four associated lenses 2302. A different number of LEDs 2307 and associated lenses 2302 may be used. An embodiment having seven LEDs and associated lenses may be particularly advantageous. This allows for LEDs to be arranged in an attractive hexagon pattern with one LED at the center in a circular flashlight head.

Figure 25:
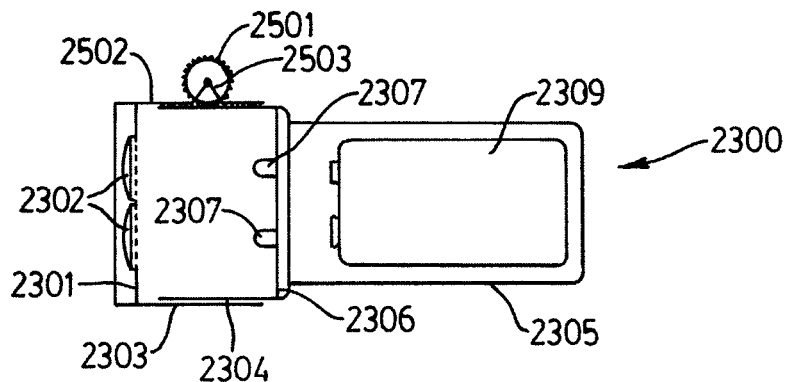
FIG. 25 is a cross sectional view of an adjustable embodiment of the light of FIG. 23.

Referring to FIG. 25, the flashlight 2300 has beam characteristics that are adjustable. The distance of the lenses 2302 from the LEDs 2307 can be adjusted by rotating a toothed thumbwheel 2501 that meshes with a toothed track 2502 on the inner head casing 2304. The thumbwheel 2501 rotates within a thumbwheel holder 2503 that is attached to the outer head casing 2303. Rotating the thumbwheel 2501 moves the outer head casing 2303 with respect to the inner head casing 2304. Since the lenses 2302 are attached to the outer head casing 2303 and the LEDs 2307 are fixed to the inner head casing 2304, moving the outer head casing 2303 with respect to the inner head casing 2304 adjusts the distance between the LEDs 2307 and their associated lenses 2302.

Figure 26:
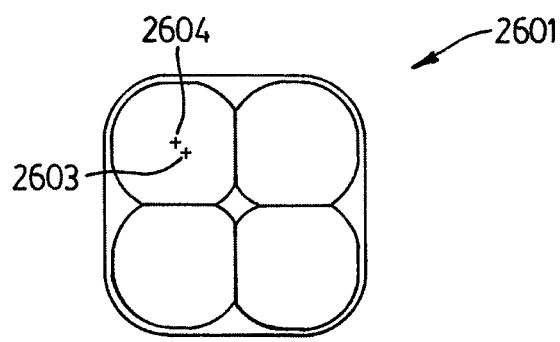
FIG. 26 is a frontal view of a lens assembly according to a preferred embodiment of the present invention.

Alternative embodiments, not shown, may utilize a round outer head casing and a round inner head casing which are threaded such that rotating the outer head casing about a common axis of the head casings can achieve adjustment of the distance between the lenses and their associated light emitting diodes. Useful degrees of rotation of the outer head casing with respect to the light emitting diodes would normally be limited to ones which place the lenses as directly forward from their light emitting diodes as possible. Referring to FIG. 26 a 1-piece molded lens assembly 2601 is similar to lens assembly 1103 of FIGS. 11 and 12. The optical centers (for example, 2603) of individual lenses 2302 may be slightly displaced from the midpoints 2604 between edges of the lenses 2302 and towards the center of the lens assembly 2601. This allows placing LEDs 2307 directly behind the midpoints between edges of their associated lenses 2302 while achieving beams that, with each other and at a finite distance forward of the lenses 2302, form these convergent beams.

Alternatively the lenses 2302 may have their optical centers at the midpoints between their edges and/or directly forward of their associated LEDs 2307. The beams formed by the lenses 2302 may be parallel and may be found to adequately converge at various finite distances forward from the lenses 2302. As a further alternative, the lens assembly 2601 may have lenses 2302 with optical centers midway between the edges of the lens elements and the LEDs 2307 may have center-to-center spacing greater than that of the lenses 2302 so that the beams produced by the lenses 2302 converge at a finite distance forward of the lens assembly 2601.

Figure 27:
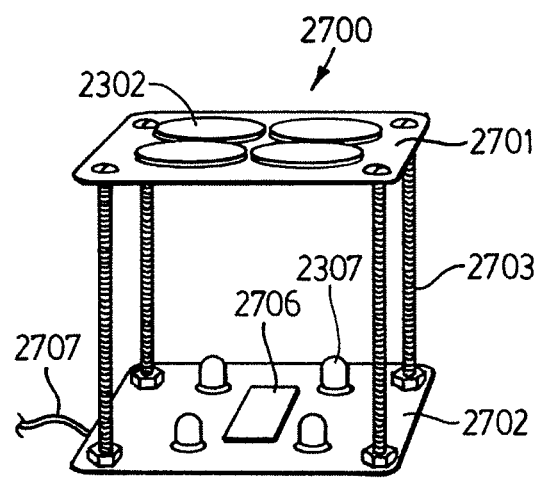
FIG. 27 is an external view showing the front, top, and left side of a lens/LED assembly according to a further preferred embodiment of the invention

Referring to FIG. 27 a light head (lens.backslash.LED assembly) 2700 is similar to lens.backslash.LED assembly 936 of FIG. 10. The head 2700 may be part of a flashlight 2300 or used as a spot light, not shown, in fixed applications, for example as an accent light or a reading light. The light head 2700 consists of a lens board 2701 and LED board 2702 attached to spacing means 2703 which maintain the proper distance between the lens board 2701 and the LED board 2702. The spacing means 2703 shown are screws, although a head casing, not shown, can be the spacing means 2703.

The other embodiments described herein may also be utilized for fixed spot light applications. In this case, "fixed" refers to situations where the spot light is not generally moved after initial set-up. Such light may have significant heat and energy savings over lights currently used in such situations. As an example, many accent lights are typically used in jewelry stores. Once the lights are put in position, the lights are not typically moved on a regular basis.

Lenses 2302 are attached to the lens board 2701 and LEDs 2307 are mounted on the LED board 2702. The lenses 2302 and the lens board 2702 may be replaced by a one-piece molded lens assembly 2601 like that shown in FIG. 26.

Current limiting circuitry 2706 may be attached to the LED board 2702. The light head 2700 receives power from a cable 2707 consisting of two wires.

The current limiting circuitry 2706 may be located elsewhere and is not necessarily attached to the structural parts shown. In some embodiments current limiting circuitry 2706 may not be necessary, such as in flashlights 2300 using batteries with internal resistance which limits the current flowing through the LEDs 2307 to a value which is not harmful to the LEDs 2307.

Embodiments can include lens 2302 center-to-center spacing greater than the LED 2307 center-to-center spacing if this is found to achieve useful beam characteristics. The lenses 2302 in the presently preferred embodiments of the invention are plano-convex with the planar surface of such lenses 2302 facing the LEDs 2307. Embodiments of the present invention may use other convergent lenses such as biconvex lenses and convex meniscus lenses and converging fresnel lenses. Embodiments of the present invention may have lens combinations to serve the purpose of each lens 2302. Compound lenses may be optimum in embodiments using LEDs 2307 that produce very wide beams.

Referring to FIGS. 28 and 29, the relationship of focal length of lens 2302 and diameter of LED 2307 are illustrated along with the size of the image 2801 that they produce. Some applications will require that the same image size must be produced at a distance that is twice that of the first design. This can be accomplished by using a lens 2901 whose focal length is twice that of lens 2302 with LED 2307 and doubling the spacing between the lens 2901 and LED 2307. The resultant spot of light or image 2902 will then be both smaller and brighter than the results obtained at this increased distance from LED 2307 and lens 2302.

Embodiments of the invention may have "zoom lenses" or other lens arrangements to simulate lenses of adjustable focal length so as to provide adjustability of the width of the beams formed by the lenses.

Alternatively, a flashlight may be supplied with different removable lens assemblies such that one lens assembly can be removed from the flashlight and a lens assembly having lenses of a different focal length can be attached to the flashlight, with the different lenses having an appropriately different distance from the LEDs 2307 according to their focal length.

Figure 30:
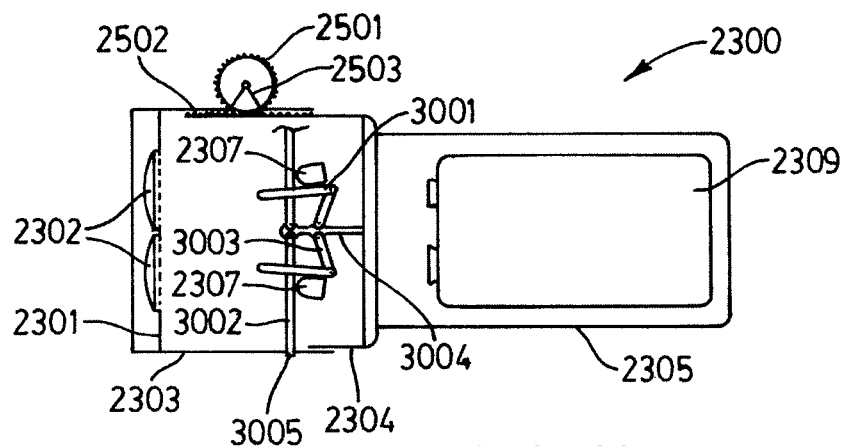
FIG. 30 is a cross sectional view of a variation of an adjustable embodiment of the light of FIG. 23.

Referring to FIG. 30, a visible light flashlight 2300 having adjustable beam characteristics and similar to the one shown in FIG. 25 is able to adjust the distance between the LEDs 2307 along with the distance between the lenses 2302 and the LEDs 2307.

The LEDs 2307 are mounted to outer movable connecting rods 3001 as opposed to being mounted to a fixed LED board. The outer movable connecting rods 3001 are connected to forward movable connecting rods 3002 and rear movable connecting rods 3003. The forward and rear connecting rods 3002 and 3003 are attached to a central axial connecting rod 3004 which is fixed to the inner head casing 2304. The forward connecting rods 3002 pass through holes 3005 in the outer head casing 2303. Some of the holes 3005 and portions of some of the forward connecting rods 3002 are not shown in order to show the toothed thumbwheel 2501 and the toothed track 2502.

The forward connecting rods 3002 and the outer connecting rods 3001 should be placed where they would not block light from the LEDs 2307.

The inner ends of the rear connecting rods 3003 are significantly more forward than the outer ends of the rear connecting rods 3003, while the forward connecting rods 3002 are more nearly perpendicular to the axial connecting rod 3004. Because of this, the LEDs 2307 are moved further from the axis of the flashlight 2300 as the outer head casing is moved forward. In addition, the outer connecting rods 3001 become less parallel to the axial connecting rod 3004 as the outer head casing is moved forward so that the LEDs 2307 remain nearly aimed at the optical centers of the lenses 2302.

As the outer head casing 2303 is moved forward, the beams formed by the lenses 2302 are not only best-focused at a distance closer to the flashlight 2300, but also nearly enough converging at the same distance. Although the arrangement shown in FIG. 30 does not perfectly accomplish convergence of the beams at the distance which they are best defined at, this arrangement can acceptably achieve adjustability in a target distance at which the beams are acceptably focused and merged together.

Variations of this arrangement and other arrangements may be found which provide a single adjustment for both beam convergence and beam focus such that the target distance can be varied with the beams acceptably converging and in focus at the target distance.

Figure 31:
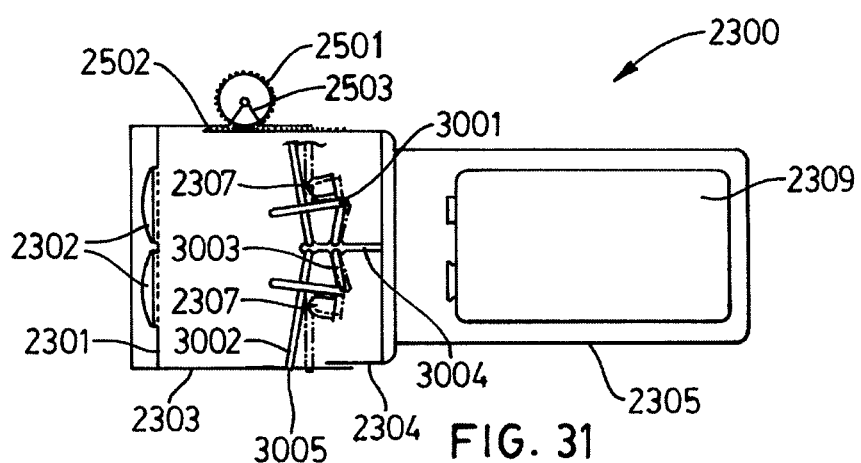
FIG. 31 is a cross sectional view of the adjustable embodiment shown in FIG. 30 as it is affected by adjustment.

Referring to FIG. 31, the adjustable version of the flashlight 2300 shown in FIG. 30 is adjusted for a shorter target distance and the beams formed by the lenses 2302 can be acceptably coinciding and converged at this shorter distance.

The outer head casing is in a more-forward position with respect to the inner head casing 2304, compared to its position shown in FIG. 30. As the outer ends of the forward connecting rods 3002 move forward along with the outer head casing 2303, the central portion of the forward connecting rods 3002 do not move with respect to the inner head casing as much as outer ends of the forward connecting rods 3002 do. Since the outer connecting rods 3001 are connected to the central portions of the forward connecting rods 3002, they and the LEDs 2307 attached to them move less with respect to the inner head casing 2304 than the outer head casing 2303 and the lenses 2302 do. In this arrangement, the spacing between the lenses 2302 and the LEDs 2307 increases as the outer head casing 2303 is moved forward with respect to the inner head casing 2304.

As the outer head casing is moved forward, the junctions between the outer connecting rods 3001 and the rear connecting rods 3003 move outward from the axial connecting rod 3004 as the angle between the axial connecting rod 3004 and the rear connecting rods 3003 decrease. The distance from the axial connection rod 3004 of the junctions between the outer connecting rods 3001 and the forward connecting rods 3002 is more constant since the forward connecting rods 3002 are shorter and more nearly perpendicular to the axial connecting rod 3004 than the rear connecting rods 3003 are.

With forward movement of the outer head casing 2303 causing the rear junction points of the outer connecting rods 3001 to move further from the axial connection rod 3004 but not causing the forward junction points of the outer connection rods to move much, the central or rear portion of the outer connection rods 3001 can be further from the axial connection rod 3004 and the outer connection rods 3001 can be less parallel to the axial connection rod 3004. This achieves position of the LEDs 2307 further from the axis of the flashlight 2300 and also achieves an increase of the angle between the axes of the LEDs 2307 and the axis of the flashlight 2300. To an acceptable extent this can achieve aim of the LEDs 2307 at the lenses and at a target at a shorter distance from the lenses 2302 as the lenses 2302 are moved further from the LEDs 2307 so that they would form a focused image of the forward surfaces of the LEDs at the shorter target distance. The previous positions of the forward connecting rods 3002, the rear connecting rods 3003 and the light emitting diodes 3004 are shown to illustrate their movement. Accordingly, the scope and spirit of the present invention includes embodiments with separate adjustments for convergence of the beams towards each other and for focusing of the beams.

Figure 32:
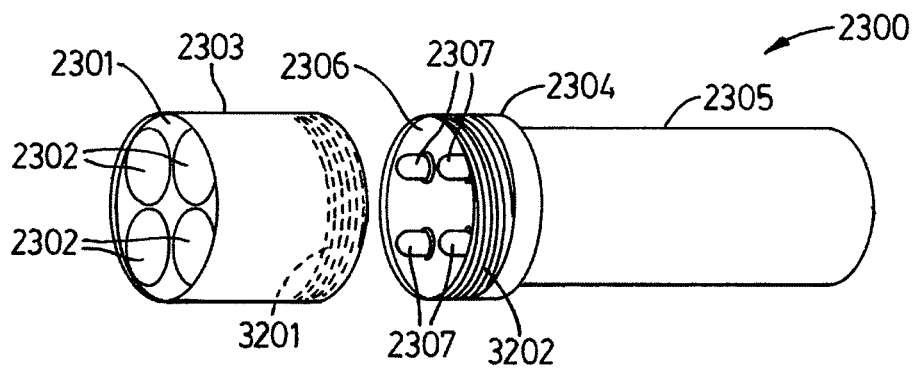
FIG. 32 is an external view of a further alternate adjustable preferred embodiment of the present invention.
Figure 33:
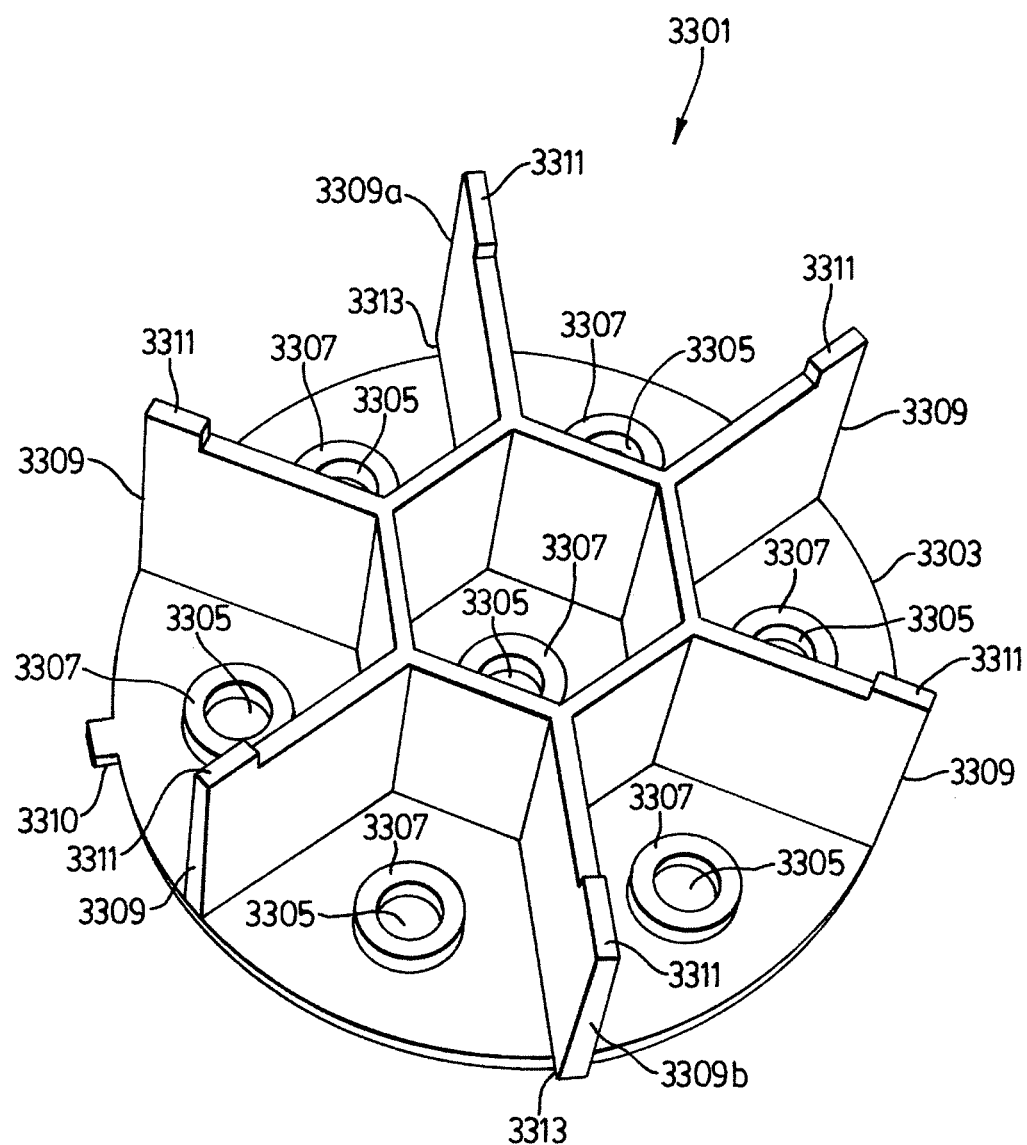
FIG. 33 is a perspective view of a baffle employed in a preferred embodiment of the present invention.

Referring to FIG. 32, the flashlight 2300 can be adjusted by rotating the outer head casing or lens collar 2303 about the inner head casing 2304. The outer head casing 2303 and the inner head casing 2304 are threaded with threads 3201 and 3202 respectively so that rotation of the outer head casing 2303 with respect to the inner head casing 2304 changes the distance of the lens board 2301 with respect to the LED board 2306.

The outer head casing 2303 is shown completely unscrewed from the inner head casing 2304 to better show the outer head casing threads 3201 and the inner head casing threads 3202.

Useful degrees of rotation will be limited to those which place each of the lenses 2302 nearly enough directly forward of one of the LEDs 2307.

Referring to FIGS. 33 through 36, an LED/lens assembly 3601 is made up of a baffle 3301, lens mount 3401, LEDs 3603 and printed circuit board 3605.

Figure 34:
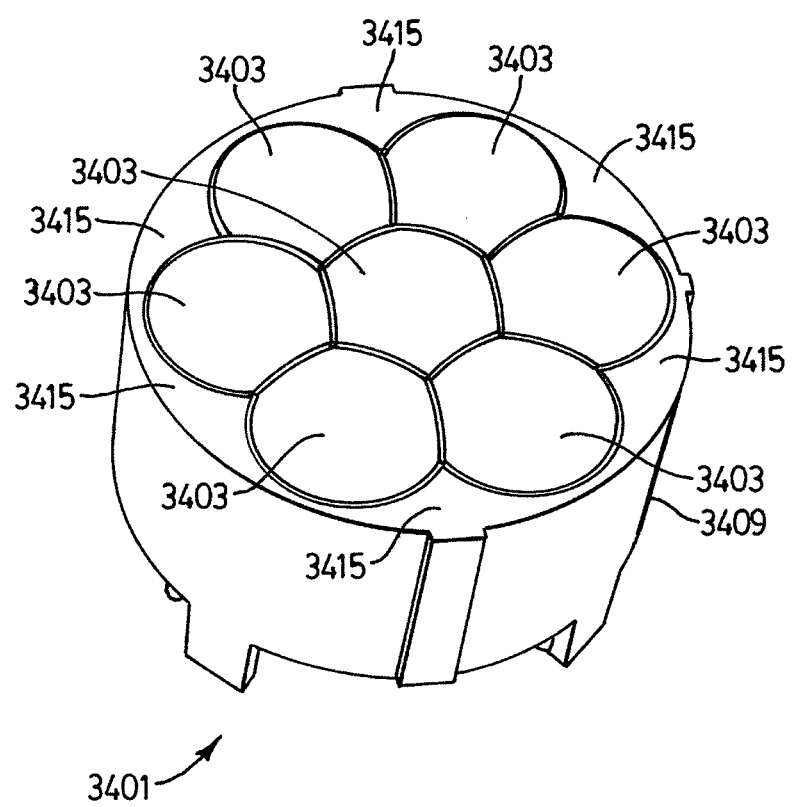
FIG. 34 is perspective view from in front of a lens mount employed in a preferred embodiment of the present invention.
Figure 35:
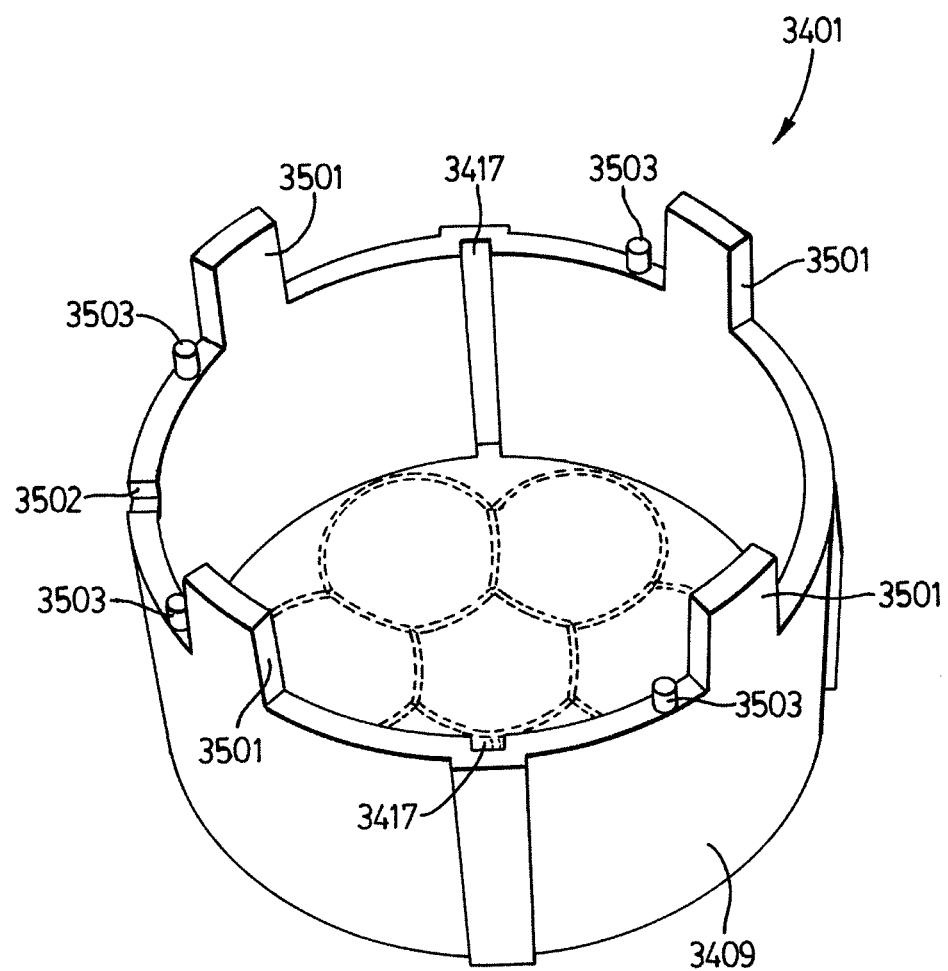
FIG. 35 is perspective from behind the lens mount of FIG. 34.
Figure 36:
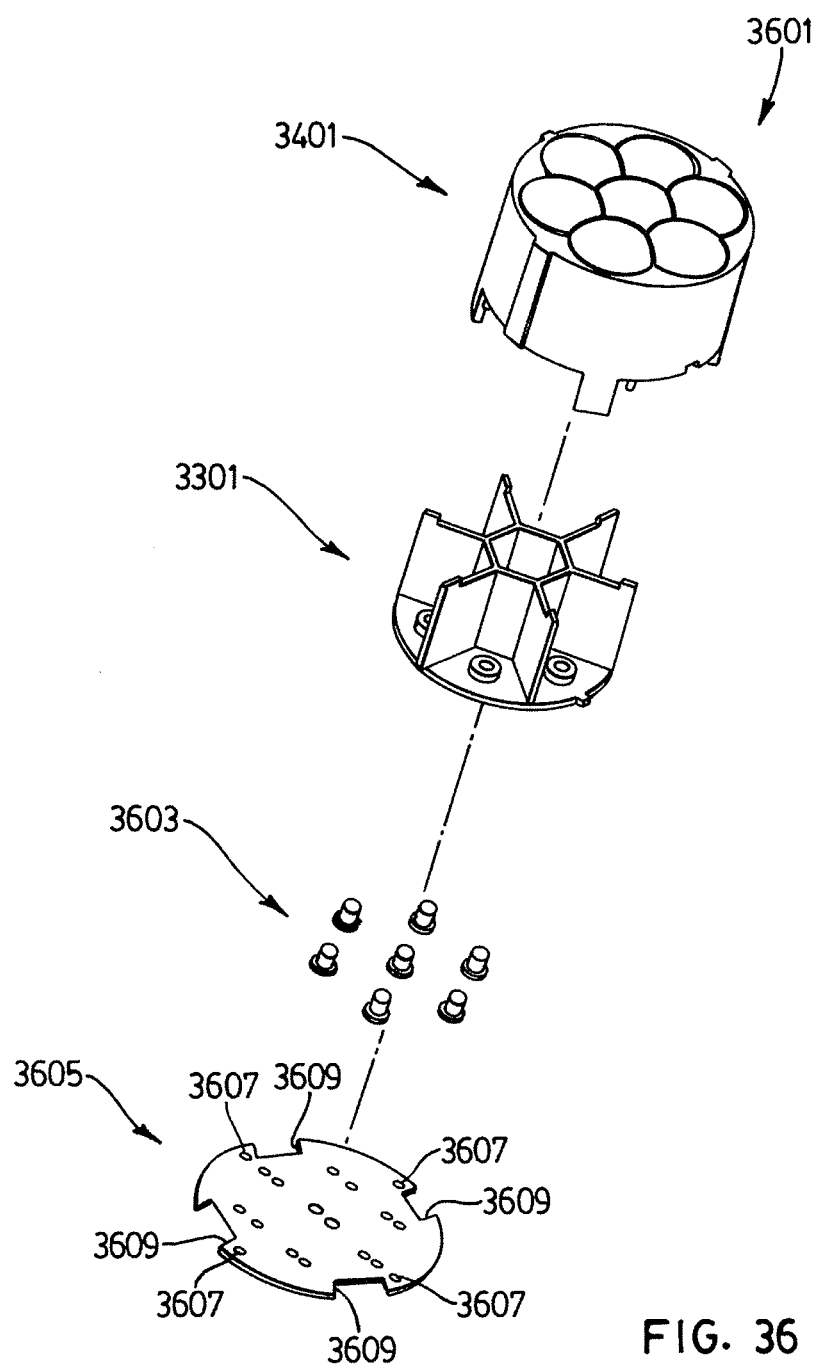
FIG. 36 is an exploded perspective view of a LED/lens assembly incorporating the baffle of FIG. 33 and the lens mount of FIG. 34 in accordance with a preferred embodiment of the invention.

The lens mount 3401 has seven lenses 3403 (FIG. 34). Six of the lens 3403 are mounted in a circular pattern with one central lens.

Correspondingly, there are seven LEDs 3603. The LEDs 3603 are mounted on the board 3605 with six LEDs 3603 evenly separated at an equal radius from center of the board 3605. One LED 3603 is mounted at the center of the board 3605. The board 3605, baffle 3301 and lens mount 3401 are circular to fit a circular profile light casing, not shown. As will be evident to the those skilled in the art using the principles described herein, other profiles may be used.

The relationship of LEDs and lenses is designed as previously set out herein, taking into account the number of LEDs and lenses used. The baffle 3301 holds the LEDs 3603 and the lens mount 3401 (and thus the lenses 3403) in the desired relationship. The baffle 3301 is also an example of a separator that prevents "cross-talk" between an LED 3603 and a non-associated lens 3403 as referred to previously herein.

The baffle 3301 has a circular base 3303 of smaller diameter then the board 3605. The base 3303 has seven circular openings 3305 spaced to receive the LEDs 3603. The openings 3305 serve to correctly space the LEDs 3603 for proper alignment with the lenses 3403. It is preferred to use a baffle or like means to space the LEDs 3603 as a LED/printed circuit board combination does not typically provide spacing within the tolerances required for alignment with the lenses 3403.

The openings 3305 have an annular extension 3307. The extension 3307 provides extra depth for proper axial alignment of the LEDs 3603.

Extending from the base 3303 are separators 3309 that separate the LEDs 3603 from one another and prevent light from one LED 3603 from passing through a lens 3403 with which it is not associated. For the particular configuration chosen the separators 3309 form a honeycomb-like pattern.

Extending outwardly from the base 3303 is a tab 3310.

The lens mount 3401 has a tubular body 3409. Enclosing one end of the tubular body 3409 is the lenses 3403. Extending from the other end of the tubular body 3409 are legs 3501. At the same end there is a notch 3502 through the tubular body 3409. The internal diameter of the body 3409 is slightly larger than the base 3303. Thus the baffle fits into the lens mount 3401 until the tab 3310 snuggly engages the notch 3502. At the same time the separators 3309 meet the lens mount 3401. The separators 3309 have extensions 3311 that engage the lens mount 3401 beneath spaces 3415 between the outer ring of lenses 3603, while not scratching the lenses 3603. This maintains a desired distance between the LEDs and their associated lenses.

The lens mount 3401 and the lenses 3603 may be formed from a single piece of plastic. Alternatively, they may be formed from multiple pieces of plastic that are fused to form a single integrated mount with lenses.

There is also a pair of opposing slots 3417 in the body 3409. Two opposing separators 3309a and 3309b extend beyond the base 3303 to form rails 3313. The rails fit within the slots 3417 for axial alignment and to prevent rotation of the baffle 3301 with respect to the lens mount 3401.

The tab 3310 and notch 3502 combination acts to orient the baffle 3301 and lens mount 3401 the same way with respect to one another at all times. Although it is intended that the baffle 3301 and the lens mount 3401 will each be symmetrical, it is possible that when manufactured they will not be symmetrical. Provided that the errors are matched in the baffle 3301 and lens mount 3401, some errors may be overcome provided that the baffle 3301 and lens mount 3401 are oriented the same way with respect to each other at all times.

Pins 3503 also extend from the tubular body 3409. There are corresponding holes 3607 in the board 3605 that engage the pins 3503. The pins 3503, sometimes referred to as heat stakes, are made from plastic. They extend through the holes 3607. The portion of the pins 3503 extending through the holes 3607 is heated to cause it to flatten out, thus retaining the board 3605 in fixed relationship to the lens mount 3401.

The legs 3501 extend through cut-outs 3609 in the board 3605. The legs 3501 are used as stand-offs from a light casing, not shown.

It will be understood by those skilled in the art that this description is made with reference to the preferred embodiment and that it is possible to make other embodiments employing the principles of the invention which fall within its spirit and scope as defined by the following claims. For example, one or more LEDs of differing beamwidth may be used. The beams do not have to be focused at the target distance. The beams may be different from one another in width or other characteristics. It may be advantageous for beams of different wavelengths to have different target areas and/or a different target distance. Any of the lenses may be fresnel lenses.

LED inspection lamps may use non-conventional LEDs such as superluminescent diodes or laser diodes.

Laser diodes used in inspection lamps may be operated in a laser mode or a non-laser mode. Laser diodes used in inspection lamps may be of types whose main application would be an associated generation of optical media that would require blue or violet laser diodes. Inspection lamps having laser diodes may have cylindrical lenses or other optics that would correct the oblong beam shape that most laser diodes have. Alternatively, laser diode beams may be collimated with non-cylindrical lenses in a scheme where non-cylindrical lenses are used to achieve a desired beam pattern.

What is claimed is:

1. An inspection lamp comprising:
   a handle;
   light emitting diodes as a source of radiation suitable for causing visible fluorescence of fluorescent materials, where said light emitting diodes are substantially non-identical in spectral characteristics of their emitted radiation, such that at least one but not all of first said light emitting diodes in said inspection lamp produce first wavelengths of radiation that are favorable for causing visible fluorescence of some fluorescent materials, and such that one or more second said light emitting diodes in said inspection lamp produce different second wavelengths of radiation which are more favorable than the wavelengths of said first said light emitting diode(s) for causing visible fluorescence of some fluorescent materials other than first said fluorescent materials; and
   a respective electrical switch each for selectively activating each type of light emitting diode as a collective group, wherein in one activation mode all of said light emitting diodes are activated wherein if one light emitting diode is emitting radiation of the first wavelengths then at least one other light emitting diode is emitting radiation of the second wavelengths, and wherein the first wavelength radiation and the second wavelength radiation emit unblocked from the lamp, and wherein in another activation mode only one type of light emitting diode is activated as a collective group.

2. An inspection lamp as set forth in claim 1 where at least one light emitting diode has a peak emission wavelength in the ultraviolet and having at least one light emitting diode with a peak emission wavelength that includes a visible narrow band suitable for causing visible fluorescence of fluorescent materials.

3. An inspection lamp as set forth in claim 1 where at least one light emitting diode produces mostly blue visible light and where at least one light emitting diode produces mostly ultraviolet radiation.

4. An inspection lamp as set forth in claim 1 where at least one light emitting diode has a peak emission wavelength in the range of 425 to 480 nanometers and at least one light emitting diode has a peak emission wavelength in the range of 360 to less than 430 nanometers.

5. An inspection lamp as set forth in claim 1 having one or more lenses to collimate the radiation produced by at least some of the light emitting diodes.

6. An inspection lamp as set forth in claim 1 where the handle shares a longitudinal axis with the inspection lamp as a whole.

7. An inspection lamp as set forth in claim 1 where the handle does not share an axis with any other major portion of said inspection lamp.

8. An inspection lamp as set forth in claim 1 designed to accept one or more dry cells as a source of power.

9. An inspection lamp as set forth in claim 1 having one or more rechargeable cells as a source of power.

10. A module having light emitting diodes that are substantially non-identical and which produce a variety of wavelengths suitable for exciting a variety of fluorescent dyes, and suitable for replacing the bulb and/or the reflector of a flashlight so as to achieve an inspection lamp as set forth in claim 1.

11. An inspection lamp as set forth in claim 1 having one or more light emitting diode modules, where at least one light emitting diode module has only one type of light emitting diode but the inspection lamp as a whole includes more than one type of light emitting diode so as to produce a variety of wavelengths suitable for exciting a variety of fluorescent dyes.

12. The inspection lamp of claim 1, further comprising a multiple element switching device which includes all of the respective electrical switches.

13. The inspection lamp of claim 12, wherein the multiple element switching device comprises a multi-pole multi-position slide switch.

14. The inspection lamp of claim 13, wherein the multi-pole multi-position slide switch comprises a two-pole multi-position slide switch.

15. A system including the inspection lamp of claim 1, further comprising at least one of said fluorescent materials having said respective visible fluorescence and which comprises a leak detection dye.

16. A light emitting diode (LED) inspection lamp, comprising:
    a handle;
    a plurality of LED sources, each source for emitting electromagnetic radiation at a different peak wavelength, each different peak wavelength for causing visible fluorescence in a different leak detection dye, and wherein one LED source produces emitting radiation of one peak wavelength and at least one other LED source produces emitting radiation of a different peak wavelength; and
    a respective electrical switch each for selectively activating each type of LED source as a collective group, wherein in one activation mode all of said LED sources are activated wherein the radiation of the one peak wavelength and the radiation of the different peak wavelength emit unblocked from the lamp, and wherein in another activation mode only one type of LED source is activated as a collective group.

17. The inspection lamp of claim 16 having at least one light emitting diode with a peak wavelength which is ultraviolet and at least one light emitting diode having a peak wavelength which is visible.

18. An inspection lamp as set forth in claim 17 having at least one light emitting diode with a peak wavelength less than 425 nanometers and at least one light emitting diode with a peak wavelength greater than 425 nanometers.

19. A system including the inspection lamp of claim 16, further comprising at least one of the leak detection dyes.

20. A light emitting diode (LED) inspection lamp, comprising:
- a handle;
- a plurality of LED sources, each source for emitting electromagnetic radiation at a different peak wavelength, each different peak wavelength for causing visible fluorescence in a different leak detection dye, and wherein each LED sources comprises a plurality of light emitting diodes; and
- a respective electrical switch each for selectively activating each type of LED source as a collective group, wherein in one activation mode all of the LED sources are activated and if one light emitting diode of one LED source is emitting radiation of one peak wavelength then at least one other light emitting diode of another LED source is emitting radiation of a different peak wavelength, and wherein the radiation of the one peak wavelength and the radiation of the different peak wavelength emit unblocked from the lamp, and wherein in another activation mode only one type of LED source is activated as a collective group.

21. A system including the inspection lamp of claim 20, further comprising at least one of the leak detection dyes.

* * * * *